(12) United States Patent
Nakagami et al.

(10) Patent No.: US 12,178,970 B2
(45) Date of Patent: Dec. 31, 2024

(54) HUB ASSEMBLY

(71) Applicant: NIPRO CORPORATION, Osaka (JP)

(72) Inventors: Hiroyuki Nakagami, Osaka (JP); Shingo Sakamoto, Osaka (JP); Haruo Akimoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 856 days.

(21) Appl. No.: 16/965,266

(22) PCT Filed: Jan. 28, 2019

(86) PCT No.: PCT/JP2019/002823
§ 371 (c)(1),
(2) Date: Jul. 27, 2020

(87) PCT Pub. No.: WO2019/146791
PCT Pub. Date: Aug. 1, 2019

(65) Prior Publication Data
US 2021/0113811 A1    Apr. 22, 2021

(30) Foreign Application Priority Data

Jan. 26, 2018 (JP) .................................. 2018-011154
Feb. 2, 2018 (JP) .................................. 2018-017286
Oct. 16, 2018 (JP) .................................. 2018-195457

(51) Int. Cl.
*A61M 25/00* (2006.01)
*A61M 5/165* (2006.01)
*A61M 5/38* (2006.01)

(52) U.S. Cl.
CPC ........ *A61M 25/0097* (2013.01); *A61M 5/385* (2013.01)

(58) Field of Classification Search
CPC .............. A61M 25/0097; A61M 5/385; A61M 39/0693; A61M 5/158; A61M 5/165;
(Continued)

(56) References Cited

U.S. PATENT DOCUMENTS 4,935,010 A * 6/1990 Cox ..................... A61M 39/045
                                                  604/167.03
5,242,411 A   9/1993 Yamamoto et al.
(Continued)

FOREIGN PATENT DOCUMENTS

JP    S63-197463 A    8/1988
JP    H04-103149 U    9/1992
(Continued)

OTHER PUBLICATIONS

Mar. 19, 2019 Search Report issued in International Patent Application No. PCT/JP2019/002823.
(Continued)

*Primary Examiner* — Robert J Utama
*Assistant Examiner* — Hamza A Darb
(74) *Attorney, Agent, or Firm* — Oliff PLC

(57) ABSTRACT

A hub assembly with a hub body connected to a tube from an external appliance, a hub outer casing which is coupled to the hub body and forms a liquid passage, a slitted separating wall disposed in the liquid passage in the hub outer casing, a filter disposed on the living body-side of the separating wall to allow the passage of gas and regulate the passage of liquid, and a ventilation passage which communicates between the liquid passage and the outside of the hub outer casing by way of the filter, wherein an end portion of the ventilation passage on the separating wall side of an opening portion facing the liquid passage is in a location at most 10 mm toward the distal end side relative to the distal end of the separating wall.

8 Claims, 21 Drawing Sheets

(58) Field of Classification Search
CPC .. A61M 25/0606; A61M 39/06; A61M 39/26; A61M 2039/205; A61M 2205/7536; A61M 2005/1402
See application file for complete search history.

(56) References Cited

U.S. PATENT DOCUMENTS

| | | | |
|---|---|---|---|
| 5,290,246 A * | 3/1994 | Yamamoto | A61M 25/0014 604/167.03 |
| 6,221,050 B1 * | 4/2001 | Ishida | A61M 25/0606 604/167.03 |
| 2005/0273019 A1 | 12/2005 | Conway et al. | |
| 2008/0194986 A1 | 8/2008 | Conway et al. | |
| 2008/0200903 A1 | 8/2008 | Christensen et al. | |
| 2010/0094171 A1 | 4/2010 | Conway et al. | |
| 2010/0204648 A1 | 8/2010 | Stout et al. | |
| 2017/0348518 A1 | 12/2017 | Ma et al. | |
| 2018/0093085 A1 * | 4/2018 | Burkholz | A61M 39/04 |

FOREIGN PATENT DOCUMENTS

| | | |
|---|---|---|
| JP | 2000-116791 A | 4/2000 |
| JP | 2001-046507 A | 2/2001 |
| JP | 2005-349195 A | 12/2005 |
| JP | 2010-508989 A | 3/2010 |
| JP | 2012-517326 A | 8/2012 |
| JP | 2016-013360 A | 1/2016 |
| JP | 2017-144028 A | 8/2017 |
| WO | 2010/093791 A1 | 8/2010 |

OTHER PUBLICATIONS

Jul. 28, 2020 International Preliminary Report on Patentability issued in International Patent Application No. PCT/JP2019/002823.
Apr. 13, 2022 Office Action issued in Chinese Patent Application No. 201980010197.8.
Sep. 23, 2021 Extended European Search Report issued in Patent Application No. 19743386.5.

* cited by examiner

⇨ AIR FLOW
➡ BLOOD FLOW

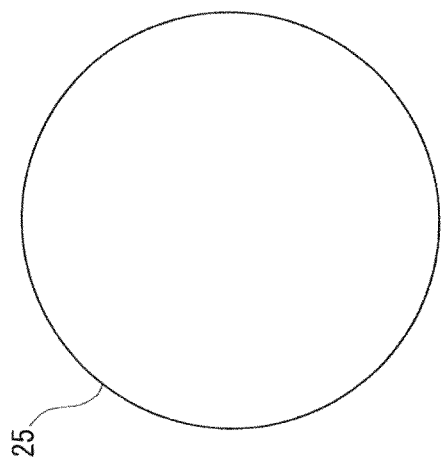
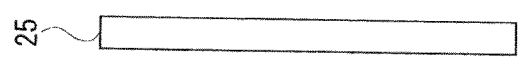

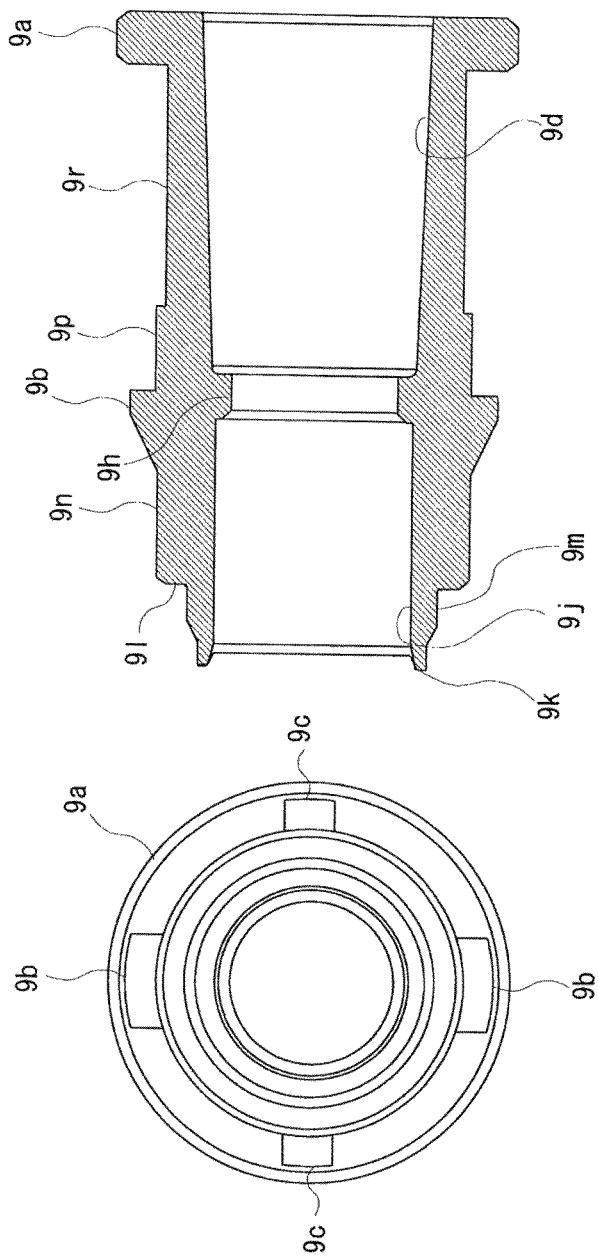

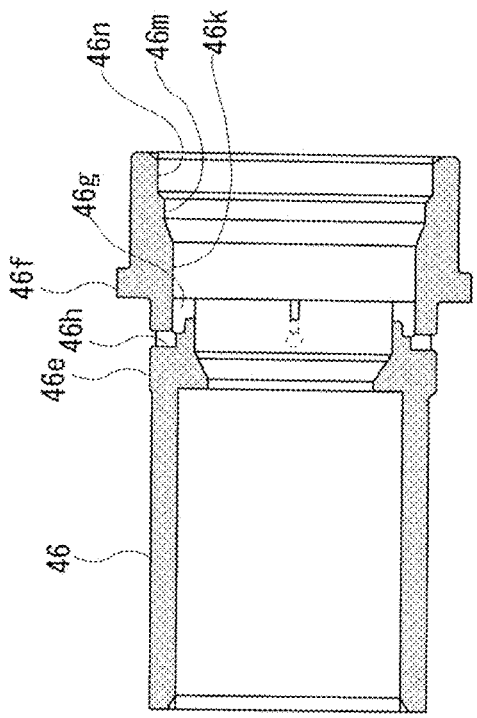
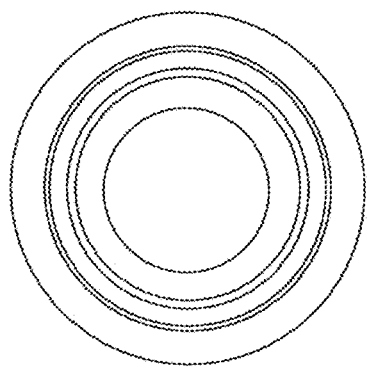
FIG.17B
FIG.17A

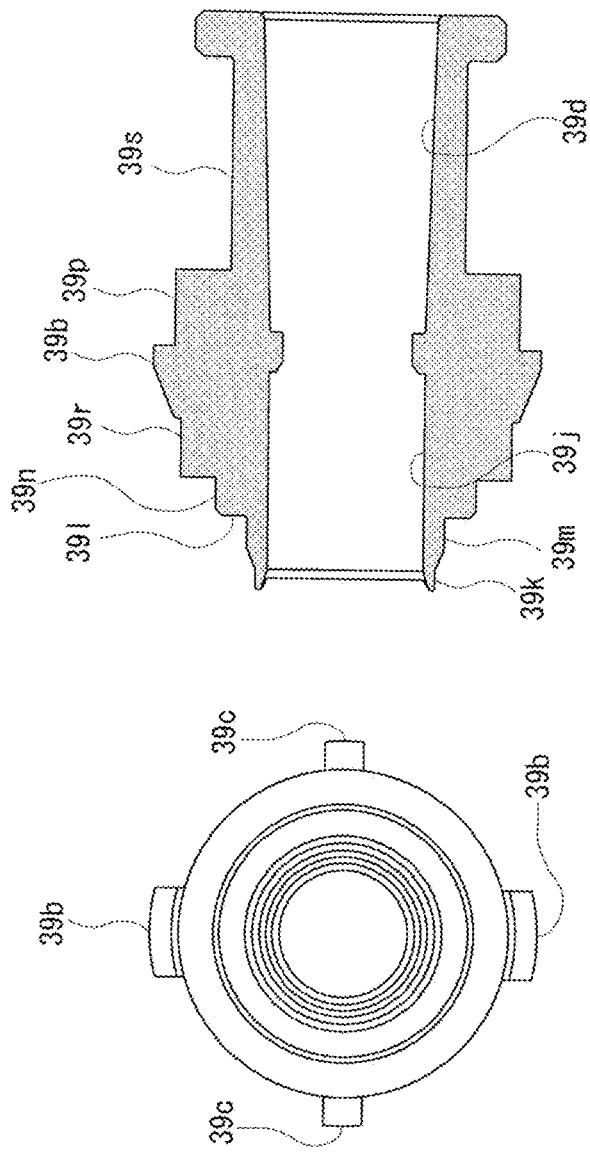

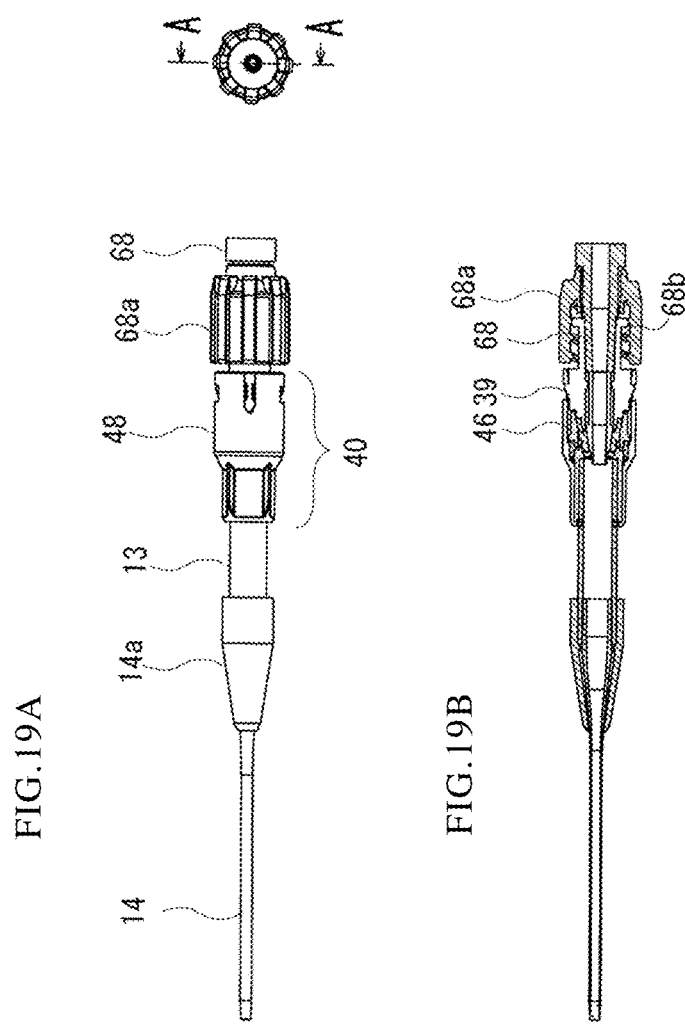

HUB ASSEMBLY

CROSS REFERENCE TO RELATED APPLICATIONS

This application is based upon and claims the benefit of priority of the prior Japanese Patent Application No. 2018-011154, filed on Jan. 26, 2018, and Japanese Patent Application No. 2018-017286, filed on Feb. 2, 2018, and Japanese Patent Application No. 2018-195457, filed on Oct. 16, 2018, and International Patent Application No. PCT/JP2019/002823, filed on Jan. 28, 2019, the entire contents of which are incorporated herein by reference.

TECHNICAL FIELD

The present invention relates to a hub assembly that is used by puncturing a blood vessel or the like during infusion, blood transfusion, artificial dialysis, etc. in a medical field.

BACKGROUND ART

Conventionally, a hub assembly having a partition wall with a slit has been known as a kind of medical tool for performing infusion, blood collection, dialysis and the like. As a relevant technique, there is known that the partition wall is formed in a disc shape, an annular recessed groove extending in the circumferential direction is formed in the partition wall, and a slit is formed in a central portion located on the inner periphery of the annular recessed groove. On the other hand, an axial distal end portion on the partition wall side of a pusher guide or an axial distal end portion on the partition wall side of the pusher is formed with a holding portion that enters into the annular recessed groove (for example, Patent Literature 1).

For such a hub assembly having the partition wall provided therein, there is known that the partition wall is further disposed in a catheter adapter of a catheter assembly, a plurality of ventilation grooves are provided between the partition wall and the inner surface of the catheter adapter, and "flashback" of blood can be made when inserting a catheter into a patient (see Patent Literature 2).

Further, there is know that a hemostatic valve, a porous seal member, and a support member are provided in the hollow portion of the catheter hub, and a blocking mechanism portion inserted and disposed on the proximal end side of the hemostatic valve allows air to flow to the proximal end side hollow portion and has a function of blocking the flow of blood to the hollow portion on the proximal end side (see Patent Literature 3).

However, in the technique of Patent Literature 2, the ventilation groove is provided between the partition wall and the inner surface of the catheter adapter, and the fluid flows toward the proximal end side of the partition wall. Therefore, there is a risk of leaking blood as well as air toward the proximal end side of the partition wall. Further, in the technique of Patent Literature 3, it is possible to circulate air in the blocking mechanism portion arranged on the proximal end side of the hemostatic valve 24 to block the flow of blood, but there is a risk of leaking blood toward the proximal end side through a gap between the joint surfaces of the members.

CITATION LIST

Patent Literature

Patent Literature 1: JP 2016-13360 A
Patent Literature 2: WO 2012-517326
Patent Literature 3: JP 2017-144028 A

SUMMARY OF INVENTION

Technical Problem

The invention has been made in view of the above circumstances, and an object of the invention is to provide a technology, in a hub assembly, which can more reliable confirm flashback of blood and prevents blood from flowing into a proximal end side of a partition wall, so that it is possible to obtain a hub assembly with higher reliability.

Solution to Problem

In the invention for solving the above-mentioned problems, there is provided a hub assembly that enables a predetermined liquid to flow between a living body to be treated or tested and an external device. The hub assembly includes a substantially cylindrical hub that is connected to a tube from the external device and forms a passage of the liquid, a partition wall that is disposed in the passage of the liquid inside the hub, a filter that allows gas in the passage of the liquid to pass therethrough and restricts passing of the liquid, and a ventilation path that communicates with the passage of the liquid and an outside of the hub through the filter, and is able to discharge the gas in the passage of the liquid to the outside by making the air pass through the filter. An end portion on the partition wall side of an opening of the ventilation path with respect to the passage of the liquid is provided at a place of 10 mm or less on a distal end side with respect to a distal end of the partition wall.

In the invention, as described above, there is provided the ventilation path which communicates the passage of the liquid and the outside of the hub through the filter, and can discharge gas in the passage of the liquid to the outside through the filter. Then, the ventilation path directly discharges the gas in the passage of the liquid on the living body side with respect to the partition wall to the outside of the hub, and blocks the liquid such as blood with the filter. Therefore, as compared with the case where only the one that connects the front and the rear of the valve in the passage of the liquid is provided as the ventilation path, the blood that has entered the passage of the liquid from the living body and is blocked by the filter is difficult to move to the external device of the partition wall. As a result, blood that has entered the passage of the liquid from the living body can be prevented from leaking to the external device side of the hub assembly. Further, in the invention, it is desirable that the ventilation path be provided with only a passage for communicating the liquid with the outside of the hub through a filter. This makes it possible to more reliably prevent the blood that has entered the passage of the liquid from leaking from the living body to the external device side of the hub assembly.

Further, in the invention, the end portion on the partition wall side of the opening of the ventilation path with respect to the passage of the liquid is provided at a place of 10 mm or less on the distal end side with respect to the distal end of the partition wall. Thus, even if air bubbles occur in the passage of the liquid, air bubbles with a size of 10 mm or more surely pass through the filter from the ventilation path and are discharged to the outside. Therefore, it is possible to prevent large air bubbles from being introduced into the living body.

Further, in the hub assembly having the ventilation path, there is an issue that blood moves in the ventilation path due to the action of the pump pressure of the external device. In the invention, there is provided a hub assembly which enables a predetermined liquid to flow between a living body to be treated or tested and an external device. The hub includes a substantially cylindrical hub that is connected to a tube from the external device and forms a passage of the liquid, a partition wall that is provided with a slit disposed in the passage of the liquid inside the hub, a filter that allows gas in the passage of the liquid to pass therethrough and restricts passing of the liquid, and a ventilation path that allows the gas in the passage of the liquid to pass through the filter for ventilation. When the tube from the external device is connected to the hub, the slit of the partition wall is pushed open to communicate a living body side and an external device side of the partition wall in the passage of the liquid. An opening of the ventilation path for the passage of the liquid on the living body side of the partition wall is provided in a region where a part of the partition wall deformed around the slit reaches when the slit of the partition wall is pushed open.

That is, in the invention, the opening of the ventilation path for the passage of the liquid is provided in a region in the inner wall of the hub, to which a part of the partition wall deformed around the slit reaches when, for example, the slit of the partition wall is pushed open by the pusher. Therefore, when the slit of the partition wall is pushed open, a part of the partition wall deformed around the slit prevents the liquid from entering the ventilation path. Therefore, in the state where the slit of the partition wall is pushed open, it is possible to prevent a pressure larger than the blood pressure of the living body from acting on the filter, such as the pump pressure of the external device, and it is possible to suppress that the blood pressure exceeds the filter due to the liquid pressure contacting the filter and the blood leaks to the outside.

As a result, conventionally, when liquid is introduced from an external device into the hub assembly and passed through the passage of the liquid, the pump pressure of the external device acts on the filter, resulting in inconveniences such as liquid leakage and shortened filter life. However, it is possible to solve these problems. In addition, if the ventilation path and the passage of the liquid are separated during dialysis treatment, it is possible to prevent the inconvenience that minute foreign substances such as thrombus that may be formed in the ventilation path are mixed into the blood vessel. In addition to the case where the ventilation path communicates the passage of the liquid of the hub assembly with the outside, the above-mentioned configuration is also applicable to a case where the ventilation path communicates the living body side of the partition wall with the external device side in the passage of the liquid of the hub assembly.

Further, in the hub assembly in which the ventilation groove is provided between the partition wall and the inner surface of the catheter adapter, the fluid flows toward the proximal end side of the partition wall. Therefore, there is an issue such as a risk of leaking blood as well as air toward the proximal end side of the partition wall. In the invention, there is provided a hub assembly that enables a predetermined liquid to flow between a living body to be treated or tested and an external device. The hub assembly includes a substantially cylindrical hub that is connected to a tube from the external device and forms a passage of the liquid, a partition wall that is provided with a slit disposed in the passage of the liquid inside the hub, a filter that allows gas in the passage of the liquid to pass therethrough and restricts passing of the liquid, a ventilation path that communicates with the passage of the liquid and an outside of the hub through the filter, and is able to discharge the gas in the passage of the liquid to the outside by making the air pass through the filter, and a filter cap that covers a region in an outer wall surface of the hub where the filter is disposed.

Here, in a case such that the filter and the ventilation path communicating the passage of the liquid and the outside of the hub through the filter are provided, in the structure where the filter is exposed on the outer surface of the hub assembly, there is a case where the filter may be damaged by being touched by human hands, or a case where the thickness of the hub cannot be sufficiently increased at the portion including the filter and the ventilation path. On the other hand, in the invention, the strength of the hub assembly can be improved by covering the hub with the filter cap. Further, it is possible to prevent inconveniences such as the user's hand touching the filter when handling the hub assembly. In addition to the case where the passage of the liquid of the hub assembly communicates with the outside as the ventilation path, the invention is also possible to apply to a case where a configuration communicating the living body side and the external device side of the partition wall in the passage of the liquid of the hub assembly is also included.

In addition, it is preferable that the filter is disposed at a position close to the opening with respect to the passage of the liquid of the ventilation path, and it is preferable that the filter is disposed closer to the living body side than the partition wall.

Further, in the invention, the hub may include a hub body connected to a tube from the external device, and a substantially cylindrical hub exterior body that is coupled to the hub body when the hub body is inserted and forms the passage of the liquid. According to this configuration, the partition wall is sandwiched and fixed by the hub body and the hub exterior body. Alternatively, the hub body may be made of a material having a hardness lower than that of the hub exterior body to prevent galling of the connector, thereby increasing the degree of freedom in designing the hub assembly.

Further, in the invention, when the slit of the partition wall is pushed open and the living body side and the external device side of the partition wall in the passage of the liquid are made to communicate, a part of the deformed partition wall may close an opening of the ventilation path with respect to the passage of the liquid. With this configuration, it is possible to more reliably prevent the pressure higher than the blood pressure of the living body from acting on the filter, and it is possible to improve the durability and reliability of the device.

Further, in the invention, the diameter of the passage of the liquid may be φ3 mm or more at a position where the opening of the ventilation path with respect to the passage of the liquid is provided. The passage of the liquid of the hub assembly according to the invention preferably has a diameter of φ1.5 mm or more in consideration of the flow rates of the liquid medicine and blood. In addition to that configuration, when the slit of the partition wall is pushed open by the pusher while the diameter of the passage of the liquid is φ3 mm or more, the diameter of a part of the partition wall deformed around the slit reaches is set. Therefore, when the pusher pushes open the slit of the partition wall, the function of closing the ventilation path by the partition wall can be more smoothly exerted. As a result, it is possible to more reliably prevent the pressure higher than the blood pressure of the living body from acting on the filter, and it is possible to improve the durability and reliability of the device.

Further, in the invention, there may be included a substantially cylindrical filter cap that covers a region in the outer wall surface of the hub exterior body where the filter is disposed. This makes it possible to improve the strength of the hub assembly even when the filter is disposed in the outer wall surface of the hub and sufficient thickness cannot be secured for the hub. Further, it is possible to prevent inconveniences such as the user's hand touching the filter when handling the hub assembly.

Further, in the invention, the filter cap may include a cap ventilation part that allows gas passed through the filter to be discharged to the outside of the filter cap. With this configuration, the air that has passed through the filter can be smoothly discharged to the outside of the filter cap, and the user can more smoothly confirm the flashback of the blood of the living body.

Further, in the invention, a part of the ventilation path may be formed by communicating a ventilation groove that is a groove provided on a passage of the liquid side as an inner wall of the hub and extends in an axial direction of the hub, and a ventilation hole that is a recess provided on an outer wall side in the hub.

According to this configuration, by changing the positional relationship between the ventilation groove and the ventilation hole and the cross-sectional shape of the ventilation groove, it becomes possible to change the mode of the ventilation path with a high degree of freedom. Further, when molding the hub including the ventilation path by resin molding, it becomes possible to increase the degree of freedom in designing the mold.

Further, in the invention, a plurality of the ventilation paths may be formed in the circumferential direction when seen from the axial direction of the hub. Preferably, the ventilation paths may be formed at least four positions at every 90 degrees. According to this configuration, even if the hub assembly is tilted, it is possible to more reliably discharge the gas to the outside of the hub through any of the ventilation paths.

Further, in the invention, the filter may have a ring-shaped three-dimensional shape provided between an outer wall surface of the hub and an inner wall surface of the filter cap. With this configuration, the filter can be easily assembled to the hub assembly. At that time, the filter may be fitted to the outer wall surface of the hub. Further, the filter need not be directly sandwiched between the outer wall surface of the hub and the inner wall surface of the filter cap, but may be indirectly sandwiched through another member.

According to this configuration, the filter can be installed on the outer wall surface of the hub by an easy method, and the structure of the hub can be simplified and the assembly can be facilitated. As a result, the cost of the device can be reduced.

Further, in the invention, at least one of corners of the outer wall surface of the hub and the inner wall surface of the filter cap, which is in contact with the filter, is rounded.

According to this configuration, when fitting the filter to the outer wall surface of the hub or when assembling the filter cap, it is possible to suppress the corners of the hub and the filter cap from coming into contact with the filter and scraping or damaging the filter. In a case where the corners are not rounded even if the filter is scraped, the shavings will remain in the corners, but if the corners are rounded, the shavings will enter and remain in the compression surface of the filter. As a result, it is possible to suppress the shavings when the filter is scraped from remaining inside the hub assembly in a state where the shavings can move.

Further, in the invention, at least a part of the filter may be compressed and fixed by the outer wall surface of the hub and the inner wall surface of the filter cap. At least a part of surroundings of the fixed filter may include a storage space for storing a protruding portion of the filter, which protrudes due to the compression of the filter.

Here, in general, when a predetermined member is compressed, the uncompressed portion of the member often projects in the opposite direction. If the above-mentioned protrusion is hindered when the member is compressed, there is a concern about inconvenience that the compression itself cannot be performed smoothly, or the pressure required for the compression increases. On the other hand, in the invention, when the filter is compressed and fixed by the outer wall surface of the hub and the inner wall surface of the filter cap, the storage space capable of storing the protruding portion of the filter is provided in advance. According to this configuration, the filter can be compressed more smoothly, and the shape and position of the filter after assembly can be stabilized.

Further, in the hub assembly in which the ventilation groove is provided between the partition wall and the inner surface of the catheter adapter, the fluid flows toward the proximal end side of the partition wall, so that there is an issue such as a risk of leaking blood as well as air toward the proximal end side of the partition wall. Further, in the hub assembly, there is an issue that the ease of assembly and the degree of freedom are improved. In the invention, there is provided a hub assembly that enables a predetermined liquid to flow between a living body to be treated or tested and an external device. The hub assembly includes a substantially cylindrical hub that is connected to a tube from the external device and forms a passage of the liquid, a partition wall that is disposed in the passage of the liquid inside the hub, a filter that allows gas in the passage of the liquid to pass therethrough and restricts the passage of the liquid, a ventilation path that communicates the passage of the liquid and an outside of the hub through the filter, and allows gas in the passage of the liquid to pass therethrough to be discharged to the outside, and a filter cap that covers a region in an outer wall surface of the hub where the filter is disposed. The hub is configured by a hub body that is connected to the tube from the external device, and a substantially cylindrical hub exterior body that is connected to the hub body from the living body side by inserting the hub body thereinto and forms the passage of the liquid. The filter cap stores at least a part of the hub exterior body and the hub body, and the hub exterior body, the hub body, and the filter cap are unified by engaging the filter cap and the hub body.

According to this configuration, the hub body can be further inserted into the hub exterior body and the filter cap by incorporating the hub exterior body inside the filter cap, and the whole can be unified by engaging the filter cap and the hub body. As a result, it is possible to reduce the number of joints as a whole, simplify the device configuration, and simplify the assembling method. Further, the unifying here means that a plurality of members are engaged with each other so that they can be handled as one body.

Further, in the hub assembly having the ventilation path, there is an issue that blood moves in the ventilation path due to pressure such as blood pressure. In the invention, there is provided a hub assembly that enables a predetermined liquid to flow between a living body to be treated or tested and an external device. The hub assembly includes a substantially cylindrical hub that is connected to a tube from the external device and forms a passage of the liquid, a partition wall that is disposed in the passage of the liquid inside the hub, and partitions a space on a distal end side and a space on a proximal end side, a filter that passes gas in the passage of the liquid, and a ventilation path that communicates the passage of the liquid with an outside of the hub or the space on the proximal end side through the filter, and passes gas in the space on the distal end side. The filter is compressed in a direction that is angled with respect to a direction in which the gas in the passage of the liquid passes through the filter.

According to the invention, the filter provided in the ventilation path is compressed and fixed in a direction in which the gas in the passage of the liquid has an angle with respect to the direction in which the gas passes through the filter. Therefore, the gap of the filter can be made small with efficiency, the pressure resistance can be improved more reliably, and the possibility of blood leaking to the outside is reduced.

Further, in the invention, it is preferable that the filter is compressed so as to be sandwiched by hard members. According to this configuration, the filter can be efficiently compressed, the gap of the filter can be more reliably reduced, and the pressure resistance can be more reliably increased.

In addition, in the hub assembly having the ventilation path, when the connector of the external device is connected to the hub, the liquid pumped by the pump of the external device keeps the momentum and flows into the opening on the distal end side from the valve of the ventilation path. Therefore, there is an issue that the liquid pumped by the pump easily flows into the ventilation path. In the invention, there is provided a hub assembly that enables a predetermined liquid to flow between a living body to be treated or tested and an external device. The hub assembly includes a substantially cylindrical hub that forms a passage of the liquid, an openable and closable partition wall that is disposed in the passage of the liquid inside the hub, and a ventilation path that includes an opening in a region on the living body side of the partition wall in the passage of the liquid, communicates the region on the living body side of the partition wall in the passage of the liquid and a region on the external device side of the partition wall in the passage of the liquid or an outside of the hub, and is able to move gas in the region on the living body side of the partition wall in the passage of the liquid to the region on the external device side of the partition wall in the passage of the liquid or the outside of the hub. When the partition wall is opened, a part of the partition wall is deformed so as to close at least a part of the opening of the ventilation path or separate the region on the living body side of the partition wall and the ventilation path.

According to this configuration, in the state where the hub assembly and the external device are connected, the liquid pumped by the pump of the external device is buffered by a part of the partition wall, so that the momentum is weakened. Therefore, it is possible to suppress the liquid from flowing into the ventilation path from the opening of the living body side region of the ventilation path. As a result, it is possible to suppress the liquid from leaking through the ventilation path. In addition, when the ventilation path communicates with the outside, it is possible to suppress a situation in which a thrombus or the like generated in the ventilation path flows into the passage of the liquid via the ventilation path.

Further, in the invention, the hub assembly may be featured in that a part of the partition wall may be deformed so as to close the entire opening of the ventilation path. According to this configuration, it is possible to surely separate the living body side region of the partition wall in the passage of the liquid from the ventilation path.

In the invention, the hub assembly may be featured in that a part of the partition wall may surround the opening of the ventilation path, or may be deformed so as to circumferentially abut on an inner surface of the hub on the living body side of the opening of the ventilation path. Further, a circumferential protrusion may be provided in a surface on the living body side of the partition wall, and the protrusion circumferentially may abut on an inner surface of the hub, so that a part of the partition wall circumferentially abuts on the inner surface of the hub on the living body side from the opening of the ventilation path.

Further, in the invention, a filter may be further provided which is provided in the middle of the ventilation path and allows the gas to pass therethrough and restricts the passage of the liquid. Although the upper limit pressure that allows the liquid to pass through varies depending on the material and compression of the filter, the liquid will pass through when the upper limit pressure is exceeded. According to this invention, it is possible to reduce that a large pressure by a pump etc. of the external device affects the filter, and to reduce the influence on the filter by a pump etc.

Further, in the invention, there is provided a hub assembly that enables a predetermined liquid to flow between a living body to be treated or tested and an external device. The hub assembly includes a substantially cylindrical hub that forms a passage of the liquid, an openable and closable partition wall that is disposed in the passage of the liquid inside the hub, and a ventilation path that includes an opening in a region on the living body side of the partition wall in the passage of the liquid, communicates the region on the living body side of the partition wall in the passage of the liquid and a region on the external device side of the partition wall in the passage of the liquid or an outside of the hub, and is able to move gas in the region on the living body side of the partition wall in the passage of the liquid to the region on the external device side of the partition wall in the passage of the liquid or the outside of the hub. A filter capable of passing gas is disposed in the ventilation path, and the filter is provided with a water absorbing swelling body.

Further, the above-described configuration can reduce a situation where blood leaks to the outside when the ventilation path communicates the passage of the liquid of the hub assembly with the outside. In addition, in a case where the ventilation path communicates the living body side of the partition wall in the passage of the liquid of the hub assembly and the external device side, it is possible to reduce the situation where blood leaks from the external device side during the time period when the connector is not inserted in the external device side of the hub assembly (when the connector is temporarily released after the inner needle is removed until the connector is connected, or a breaking in the rest room).

In the invention, modes for solving the above problems can be used in combination as much as possible.

Advantageous Effects of Invention

According to the invention, in a hub assembly, it is possible to confirm the flashback of blood and obtain higher reliability.

BRIEF DESCRIPTION OF DRAWINGS

FIG. 6A and FIG. 6B are schematic diagrams of a filter in an embodiment of the invention.

FIG. 7A and FIG. 7B are schematic diagrams of a guide connector in an embodiment of the invention.

FIG. 17A and FIG. 17B are schematic diagrams of a connector cover in the third embodiment of the invention.

FIG. 18A and FIG. 18B are schematic diagrams of a guide connector in the third embodiment of the invention.

FIG. 19A and FIG. 19B are diagrams illustrating a state in which a connector is attached to the outer needle unit according to the third embodiment of the invention, and a cross-sectional view as seen from a direction perpendicular to an axis.

DESCRIPTION OF EMBODIMENTS

Hereinafter, embodiments of the invention will be described with reference to the drawings. Further, the following embodiments are merely examples of the modes for carrying out the invention, and do not particularly limit the configuration of the invention.

First Embodiment

<Basic Configuration>

Figure 1A:
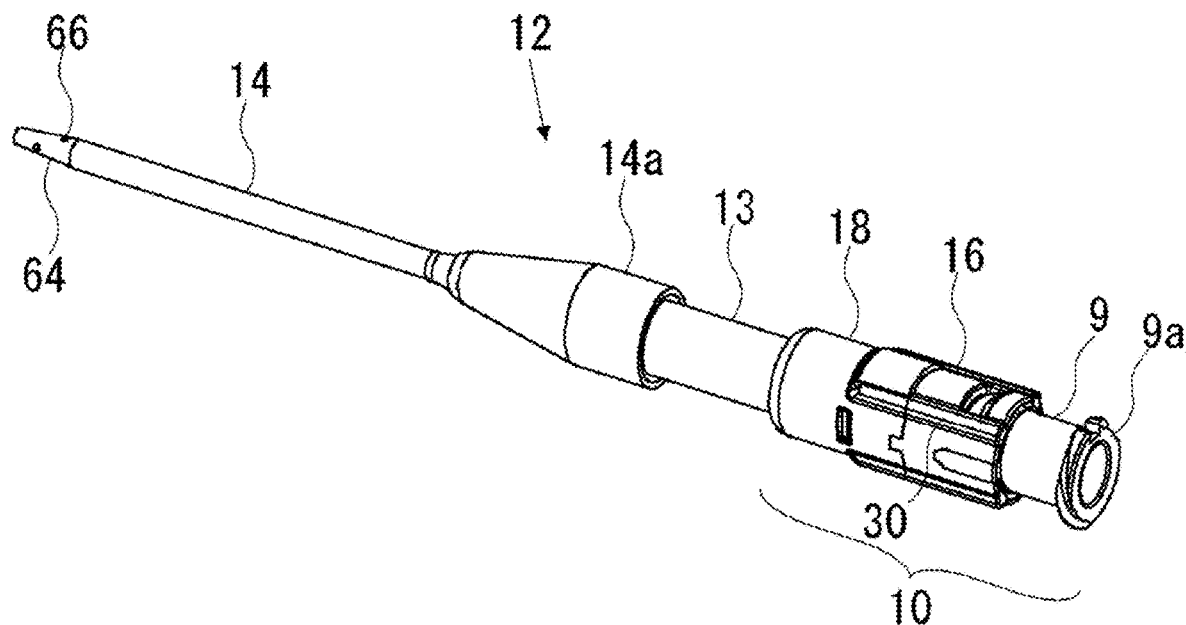
FIG. 1A and FIG. 1B are perspective views of an outer needle unit according to an embodiment of the invention.
Figure 1B:
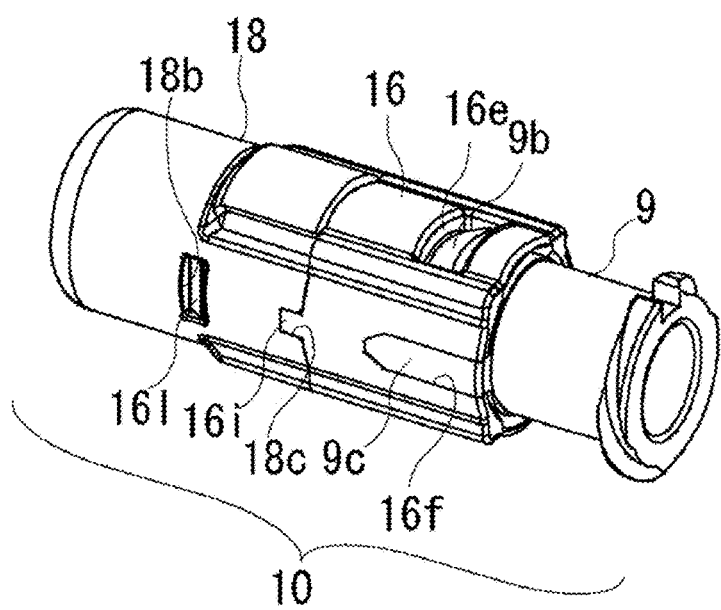
Figure 2:
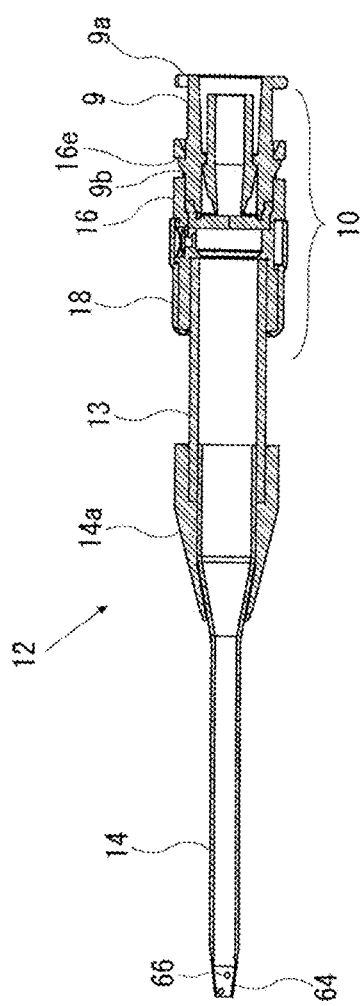
FIG. 2 is a cross-sectional view of an outer needle unit according to a first embodiment of the invention as seen from a direction perpendicular to an axis.

FIGS. 1 and 2 illustrate an outer needle unit 12 in an indwelling needle assembly including a hub assembly 10 according to an embodiment of the invention. FIG. 1A is a perspective view of the outer needle unit 12, and FIG. 1B is an enlarged view of a perspective view of the hub assembly 10 in particular. FIG. 2 is a cross-sectional view of the outer needle unit 12 as seen from a direction perpendicular to the axial direction. In the present specification, the axial direction is the length direction of the fluid passage formed by the outer needle unit 12, and means the left-right direction in FIG. 2. Further, the distal end side means the left side in FIG. 2, and the proximal end side means the right side in FIG. 2.

In the outer needle unit 12 illustrated in FIG. 1, the proximal end of a cylindrical clamping tube 13 is fixed to the distal end side of the hub assembly 10, and a hollow outer needle 14 and an outer needle base 14a which is provided with the diameter of the proximal end side of the outer needle 14 expanded are fixed to the distal end side of the clamping tube 13. In addition, a tapered outer peripheral surface 64 is formed at the distal end portion of the outer needle 14 to reduce puncture resistance to a living body, and a plurality of through holes 66 are provided in the peripheral wall of the tapered outer peripheral surface 64 to improve the flow efficiency of the fluid with respect to the outer needle 14. Then, a known inner needle unit including an inner needle is inserted into the outer needle unit 12 to form the indwelling needle assembly.

A schematic shape of the hub assembly 10 is formed by inserting a guide connector 9 which is an example of a hub body into a proximal end side of a connector cover 16 which is an example of a hub exterior body. The connector cover 16 has a substantially cylindrical shape. Further, on the outer wall surface of the connector cover 16 on the proximal end side, a plurality of ridges 30 are formed in parallel with the axial direction so that the user can easily grip. A lock portion 9a provided with a screw thread is formed on the outer wall surface of the proximal end side opening of the guide connector 9, and is configured to connect a luer lock type of male connector to the proximal end side opening of the guide connector 9. Further, in this embodiment, a filter cap 18 having a substantially cylindrical shape and covering a region on the distal end side of the connector cover 16 is attached to the distal end side of the connector cover 16.

Figure 3:
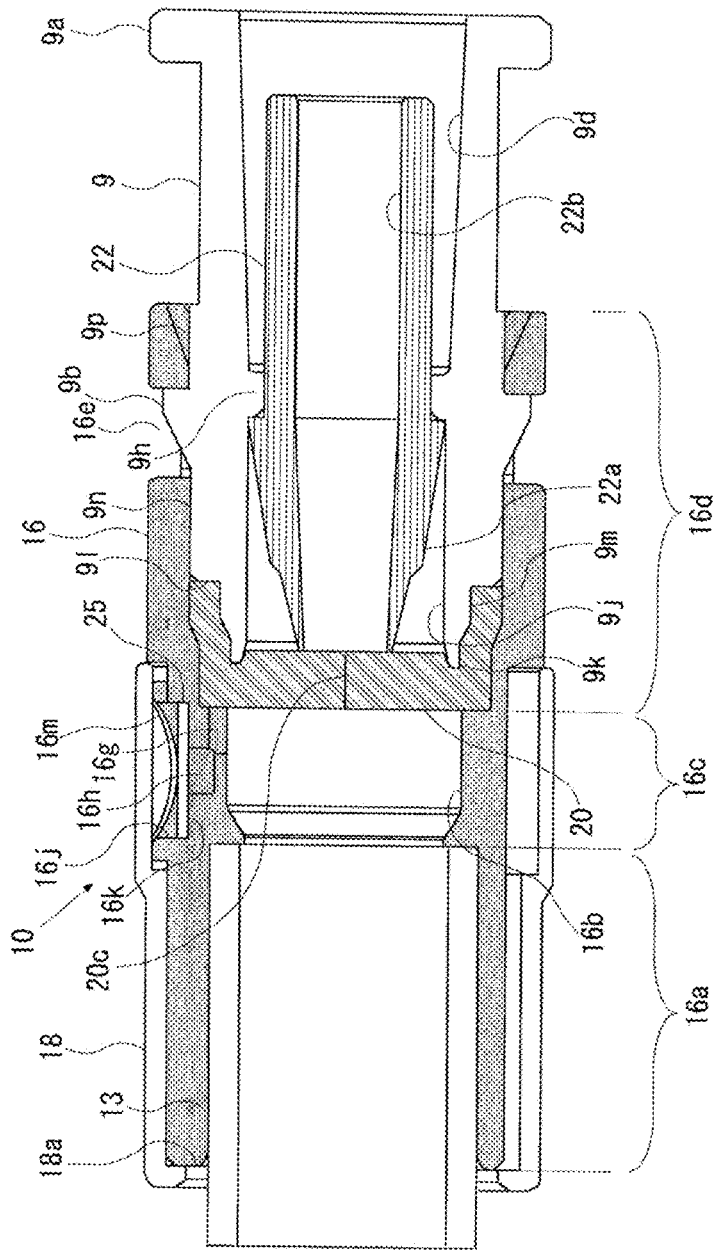
FIG. 3 is a cross-sectional view of a hub assembly according to the first embodiment of the invention as seen from a direction perpendicular to an axis.

Next, the structure of the hub assembly 10 will be described in more detail with reference to FIG. 3. FIG. 3 is a cross-sectional view of the hub assembly 10 as seen from a direction perpendicular to the axial direction. Inside the connector cover 16, a distal-end fitting portion 16a that forms a cylindrical space into which the clamping tube 13 is fitted is provided on the distal end side. A proximal-end insertion portion 16d that forms a substantially cylindrical space is provided on the proximal end side so as to insert and fix the guide connector 9. Further, a connection wall portion 16c is provided that forms a communication hole 16b having a circular cross section to communicate between the distal-end fitting portion 16a and the proximal-end insertion portion 16d.

As described above, the clamping tube 13 is press-fitted and fixed to the distal-end fitting portion 16a from the distal end side. Further, the guide connector 9 is inserted into the proximal-end insertion portion 16d, and a position restricting claw 9b engages with an engagement hole 16e of the connector cover 16 to prevent detachment. Further, as illustrated in FIG. 1B, a position restricting convex portion 9c engages with an engagement slit 16f of the connector cover 16, so that excessive movement of the guide connector 9 toward the distal end side of the connector cover 16 or rotation around the axis is restricted.

Further, the region on the distal end side of the outer wall surface of the connector cover 16 is covered with the filter cap 18 having a substantially cylindrical shape. The diameter of the filter cap 18 is reduced at its distal end, and a step 18a at the distal end of the reduced diameter is brought into contact with the distal end of the connector cover 16 to restrict movement toward the proximal end side. Further, as illustrated in FIG. 1B, a cap position restricting claw 161 provided in the connector cover 16 engages with a cap engaging hole 18b of the filter cap 18, so that the detachment of the filter cap 18 is restricted with respect to the connector cover 16. Further, a cap position restricting convex portion 16i provided in the connector cover 16 engages with a cap engaging slit 18c of the filter cap 18, so that excessive movement of the connector cover 16 toward the proximal end side of the filter cap 18 or rotation around the axis is restricted.

Figure 4A:
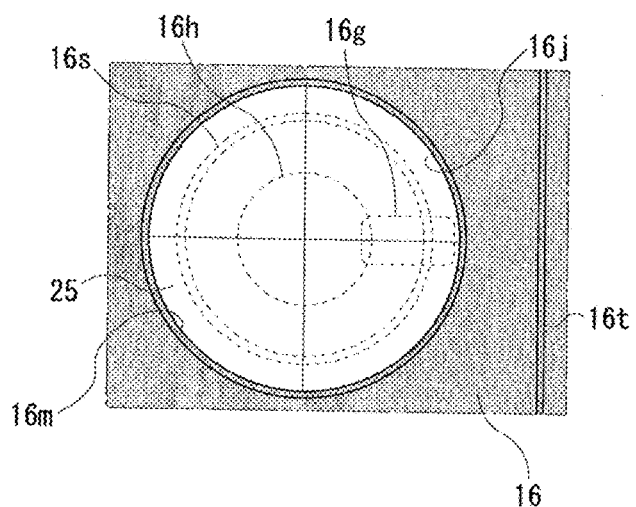
FIG. 4A and FIG. 4B are diagrams illustrating the vicinity of a filter in the hub assembly according to the first embodiment of the invention.
Figure 4B:
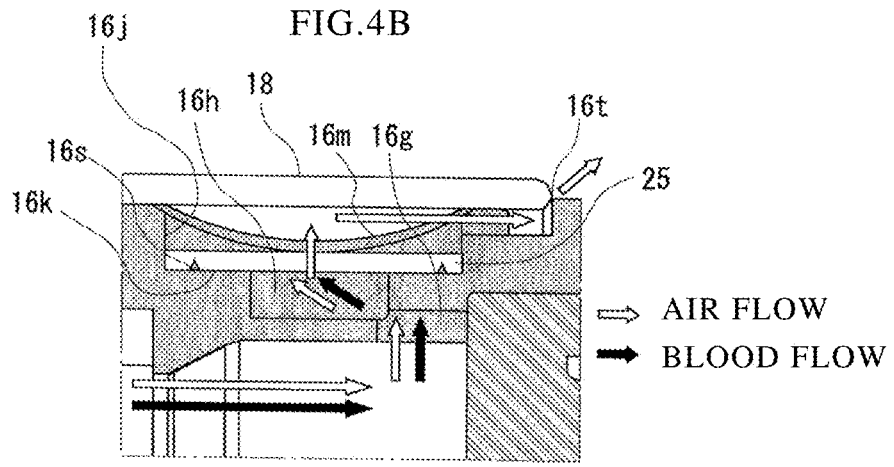

FIG. 4 illustrates a diagram around the filter 25 (described later) in the hub assembly 10. FIG. 4A is a view as seen from the axial direction of the filter 25 (described later), and FIG. 4B is a cross-sectional view as seen from a direction perpendicular to the axis of the filter 25 (described later). Further, in this embodiment, the filter cap 18 is made of a transparent resin material, so that it is not illustrated in FIG. 4A. As illustrated in FIGS. 3 and 4, in the connector cover 16, a filter storage portion 16j is provided in the outer wall of a region that is covered with the filter cap 18 and that corresponds to the communication hole 16b in the axial direction. The filter storage portion 16j is a cylindrical space having a circular cross section when viewed from a direction perpendicular to the axis of the connector cover 16. The filter storage portion 16j opens at a filter opening 16m of the outer wall surface of the connector cover 16.

A disc-shaped filter 25 is installed on a filter installation surface 16k that is the bottom surface of the cylindrical filter storage portion 16j. The filter 25 is a membrane filter made of a porous film made of fluororesin, cellulose acetate, polyethylene, acrylic, polyether sulfone, glass fiber or the like. FIG. 6 illustrates a schematic shape of the filter 25. Further, a ventilation hole 16h, which is a cylindrical recess, is provided in the center of the filter installation surface 16k. In addition, the filter 25 is fixed to the filter installation surface 16k by welding at a welding portion 16s so as to surround the opening of the ventilation hole 16h with no gap.

On the other hand, the inner wall surface of the communication hole 16b in the connector cover 16 is provided with a ventilation groove 16g for allowing the air in the communication hole 16b to escape to the outside. The ventilation groove 16g is a recessed groove provided in the inner wall surface of the communication hole 16b and extending in the front-rear direction. A part of the ventilation groove 16g on the distal end side communicates with the above-described ventilation hole 16h. Therefore, the air in the communication hole 16b can pass through the filter 25 through the ventilation groove 16g and the ventilation hole 16h, and can flow out through a gap 16t between the connector cover 16 and the filter cap 18 to the outside. On the other hand, the liquid such as blood existing in the communication hole 16b reaches the filter 25 through the ventilation groove 16g and the ventilation hole 16h, but is blocked by the filter 25 and prevented from leaking to the outside. In this embodiment, the gap 16t between the connector cover 16 and the filter cap 18 is an example of a cap ventilation part. Further, in this embodiment, the positions of the ventilation groove 16g and the ventilation hole 16h are deviated. With this configuration, the ventilation groove 16g can be adjacent to the partition wall while maintaining the moldability of the hub, but the ventilation groove 16g and the ventilation hole 16h may be aligned with each other.

Figure 5A:
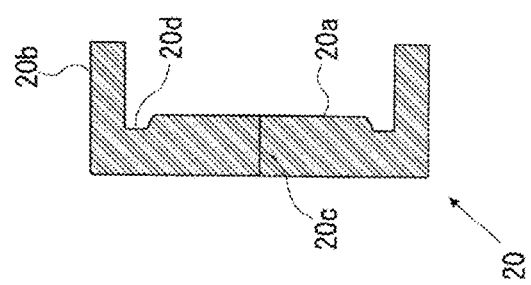
FIG. 5A and FIG. 5B are schematic diagrams of a disc valve according to an embodiment of the invention.
Figure 5B:
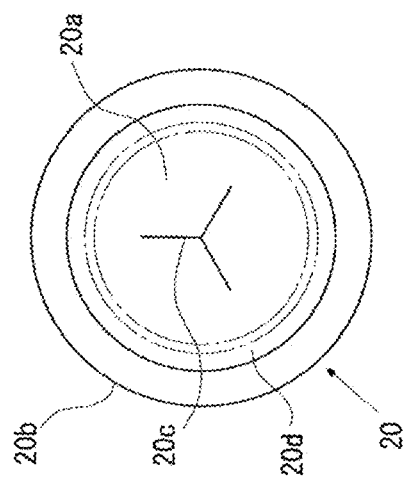

As illustrated in FIG. 3, inside the connector cover 16, a disc valve 20 as a partition wall having a slit 20c is mounted. FIG. 5 illustrates a schematic configuration of the disc valve 20. FIG. 5A is a cross-sectional view as seen from a direction perpendicular to the axial direction, and FIG. 5B is a view as seen from the proximal end side. The disc valve 20 includes a disc-shaped disc portion 20a and a frame-shaped frame portion 20b provided in the outer periphery of the disc portion 20a and protruding toward the proximal end side. The disc portion 20a is provided with slits 20c radially provided at intervals of 120 degrees from the center of the disc portion 20a, and an annular groove 20d is provided at a boundary portion between the disc portion 20a and the frame portion 20b. Further, the frame portion 20b is formed continuously over the entire circumference in the circumferential direction to have a substantially cylindrical shape, and is formed such that the wall portion on the outer peripheral side of the groove 20d is directly extended to the proximal end side.

The disc valve 20 is a disc-shaped valve body that is elastically deformable by being formed of rubber or elastomer. Further, the slit 20c may have a linear shape, a cross shape, or a radial shape extending from the center in four or more directions.

The description returns to FIG. 3. The disc valve 20 is inserted into the proximal-end insertion portion 16d of the connector cover 16, the surface on the distal end side of the disc portion 20a is brought into contact with the connection wall portion 16c, and the outer wall surface of the frame portion 20b is brought into contact with the inner wall surface near the connection wall portion 16c in the proximal-end insertion portion 16d, so that the position is restricted. Here, the outer diameter dimension of the disc valve 20 in a single item state is slightly larger than the inner diameter dimension of the proximal-end insertion portion 16d of the connector cover 16 near the connection wall portion 16c. As a result, in the state where the disc valve 20 is assembled to the connector cover 16, a radial compressive force is exerted on the disc valve 20 and a stress for holding the slit 20c in the closed state is given. Further, when the disc valve 20 is accommodated and mounted in the connector cover 16, the groove 20d is opened toward the proximal end side in the axial direction.

On the proximal end side of the disc valve 20, a substantially cylindrical pusher 22 is arranged. The pusher 22 includes an inner wall surface 22b that forms an insertion hole extending linearly over the entire length in the axial direction. Further, the outer wall surface on the distal end side of the pusher 22 is a tapered portion 22a having a diameter gradually decreasing toward the distal end side, and the pusher 22 is pushed into the slit 20c of the disc valve 20 by advancing, and the distal end side and of the proximal end side of 20 are communicated with each other. Further, the outer wall surface of the proximal end side portion of the pusher 22 has a smaller diameter than the maximum outer diameter dimension of the tapered portion 22a.

The guide connector 9 is a substantially cylindrical member. At the installation position, the distal end portion 9k of the guide connector 9 enters the groove 20d of the disc valve 20 and presses the groove 20d against the wall surface of the connection wall portion 16c in the proximal-end insertion portion 16d of the connector cover 16, thereby restricting the position and orientation of the disc portion 20a. Further, these may be in contact with each other with zero touch, or may be pressed to compress the outer peripheral end portion of the disc valve 20 in the axial direction. Further, on the outer wall surface of the distal end portion 9k on the proximal end side, a diameter-expanded surface 9m that is expanded in a tapered shape in diameter is formed. The outer wall surface of the diameter-expanded surface 9m pushes the inner wall surface of the frame portion 20b of the disc valve 20. Then, the frame portion 20b of the disc valve 20 is radially sandwiched between the inner wall surface of the proximal-end insertion portion 16d of the connector cover 16 and the outer wall surface of the diameter-expanded surface 9m of the guide connector 9 to support the disc valve 20. With this configuration, air-tightness and liquid-tightness between the outer wall surface of the disc valve 20 and the inner wall surface of the connector cover 16 are secured.

Further, a vertical surface 9l which is a wall surface vertically raised on the outer peripheral side is provided on the proximal end side of the diameter-expanded surface 9m of the guide connector 9. This vertical surface 9l presses the end portion of the frame portion 20b of the disc valve 20 on the proximal end side toward the distal end side when the guide connector 9 is assembled. Therefore, the frame portion 20b of the disc valve 20 is axially sandwiched between the wall surface of the connection wall portion 16c of the connector cover 16 and the vertical surface 9l of the guide connector 9, which also supports the disc valve 20. This ensures the air-tightness and the liquid-tightness between the outer wall surface of the disc valve 20 and the inner wall surface of the connector cover 16.

On the inner wall surface 9j of the guide connector 9, a step portion 9h protruding toward the inner peripheral side is formed in an annular shape continuous in the circumferential direction. The inner diameter dimension of the step portion 9h is set to be substantially the same as or slightly larger than the diameter dimension of the outer wall surface of the proximal end side portion of the pusher 22. The inner diameter dimension of the inner wall surface 9j of the guide connector 9 is substantially equal to or slightly larger than the maximum outer diameter dimension of the tapered portion 22a in the pusher 22. As a result, the inner wall surface of the step portion 9h holds the outer wall surface of the proximal end side portion of the pusher 22, and the maximum outer diameter portion of the tapered portion 22a of the pusher 22 is held by the inner wall surface 9j of the guide connector 9. As a result, the pusher 22 is supported and guided in the guide connector 9 substantially coaxially. Further, the inner diameter dimension of the step portion 9h is set smaller than the maximum outer diameter of the tapered portion 22a in the pusher 22. As a result, the pusher 22 is prevented from moving toward the proximal end side and coming off the guide connector 9.

In the assembled state, it is preferable that the surface on the proximal end side of the disc portion 20a of the disc valve 20 and the distal end of the pusher 22 are in contact with each other. Thereby, the position of the distal end side of the pusher 22 can be defined, the pusher 22 can be positioned in the axial direction between the disc valve 20 and the guide connector 9, and the risk that the pusher 22 is tilted with respect to the axial direction can be reduced.

FIG. 7 illustrates a schematic diagram of the guide connector 9 in this embodiment. FIG. 7A is a view as seen from the distal end side in the axial direction, and FIG. 7B is a cross-sectional view as seen from a direction perpendicular to the axial direction. The guide connector 9 in this embodiment has a substantially cylindrical shape as a whole as described above, and a region 9d on the proximal end side of the inner wall surface is a tapered surface whose diameter increases toward the proximal end side. This taper angle is set to match the taper angle of the connector at the distal end of the tube from an external device such as a dialyzer.

When the guide connector 9 is inserted into the connector cover 16, the position restricting claw 9b is engaged with the engagement hole 16e of the connector cover 16, and the position restricting convex portion 9c is engaged with the engagement slit 16f of the connector cover 16, the position of the guide connector 9 in the connector cover 16 is determined.

Further, a cover insertion surface 9n facing the inner wall surface of the connector cover 16 is provided on the proximal end side of the vertical surface 9l in the outer wall surface of the guide connector 9. The cover insertion surface 9n has an outer diameter to be slightly smaller than the inner wall surface of the connector cover 16, and can stably maintain the position and inclination in the direction perpendicular to the axis of the guide connector 9 in the connector cover 16.

A second cover insertion surface 9p facing the inner wall surface on the proximal end side from the engagement hole 16e of the connector cover 16 is provided on the proximal end side of the position restricting claw 9b in the outer wall surface of the guide connector 9. The second cover insertion surface 9p has an outer diameter to be slightly smaller than the inner wall surface of the engagement hole 16e in the connector cover 16 on the proximal end side, and helps the maintenance of the position and inclination in the direction perpendicular to the axis of the guide connector 9 in the connector cover 16.

An exposed surface 9r, which is a portion exposed to the proximal end side of the connector cover 16, is provided further on the proximal end side of the second cover insertion surface 9p on the outer wall surface of the guide connector 9. The outer wall surface of this exposed surface 9r has a diameter to be smaller than the cover insertion surface 9n and the second cover insertion surface 9p, and ensures workability when connecting the connector at the distal end of the tube from an external device to the guide connector 9.

Figure 8:
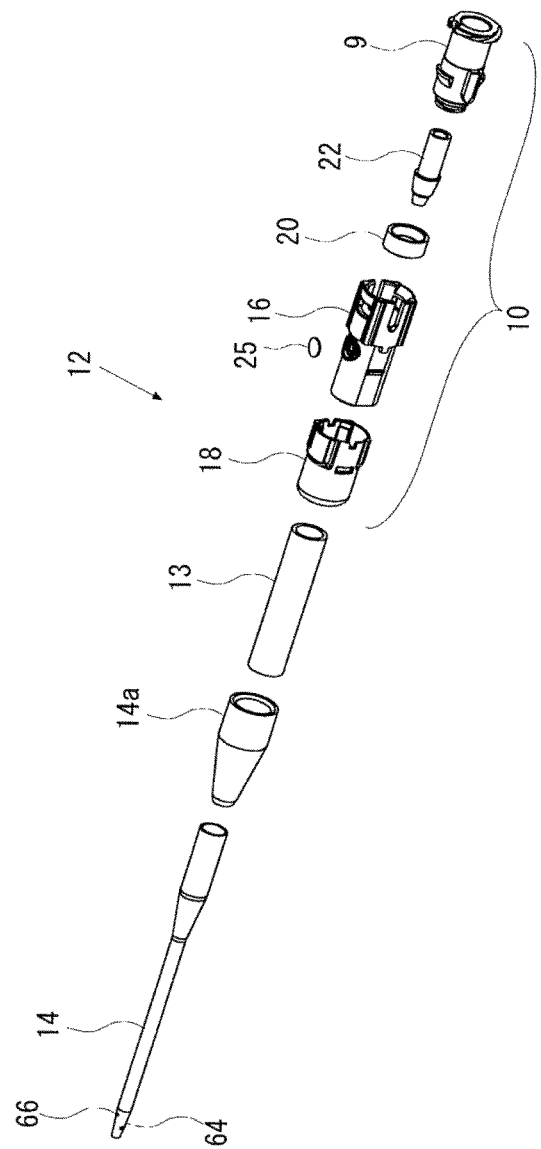
FIG. 8 is an exploded perspective view of the outer needle unit in an embodiment of the invention.

Further, the connector cover 16, the guide connector 9, and the pusher 22 described above may be formed of a material having rigidity that allows the initial shape to be maintained without being substantially deformed by an external force that acts. Preferably, a hard synthetic resin material may be employed. For example, polycarbonate, polyamide, polysulfone, polyarylate, or the like may be used. Further, the material forming the guide connector 9 may be lower in hardness than the material forming the connector cover 16. By doing so, it is possible to suppress the galling between the guide connector 9 and the connector from the external device while ensuring the strength of the entire hub assembly. FIG. 8 illustrates an exploded perspective view of the outer needle unit 12 in this embodiment.
<Operations>

The outer needle 14, the outer needle base 14a, and the clamping tube 13 are fixed to the distal end of the hub assembly 10 having the above-described structure, thereby forming the outer needle unit 12. The outer needle 14 may be a conventionally known one, and may be a metal hollow needle formed of, for example, stainless steel, but may be formed by a material having appropriate flexibility, for example, various soft resins.

Further, an indwelling needle assembly is constructed by inserting an inner needle unit (not illustrated) having an inner needle into the outer needle unit 12. Here, by inserting the inner needle unit into the outer needle unit 12, the inner needle is inserted into the slit 20c of the disc valve 20, but the pusher 22 is in the assembled state illustrated in FIG. 3 and the like. Therefore, the disc valve 20 is not largely elastically deformed.

When using the indwelling needle assembly described above, first, after puncturing the blood vessel of the living body with the indwelling needle assembly, it is confirmed that the inner needle unit is punctured in the blood vessel, and the inner needle unit is pulled out from the outer needle unit 12 to the proximal end side. As a result, the outer needle unit 12 can be indwelled while being punctured to the blood vessel of the patient. At that time, the inner needle is removed from the disc valve 20, whereby the disc valve 20 is restored to the initial shape, and the slit 20c is closed.

At this time, for example, the air existing in the clamping tube 13 is pushed out toward the proximal end side by the inflow pressure of blood. This air flows into the ventilation groove 16g provided in the inner wall surface of the connector cover 16. Then, the air further flows into the ventilation hole 16h and reaches the filter 25. Since the filter 25 is configured to pass air (gas), the air can be discharged as it is into the space between the filter cap 18 and the connector cover 16. Further, the air is discharged to the outside through the gap 16t between the filter cap 18 and the outer wall surface of the connector cover 16. As a result, the air can flow out from the inside of the clamping tube 13 to the outside through the communication hole 16b, the ventilation groove 16g, the ventilation hole 16h, the filter 25, and the gap 16t between the connector cover 16 and the filter cap 18. As a result, the outer needle 14 and the clamping tube 13 are filled with blood. By visually recognizing the "flashback", the user can confirm that the outer needle unit 12 is normally punctured into the blood vessel of the living body.

When the inner needle comes off from the disc valve 20, the blood fills the clamping tube 13 and a part of the blood flows into the communication hole 16b, the ventilation groove 16g, and the ventilation hole 16h, but is disturbed from flowing out to the outside by the filter 25. Further, since the diameter-expanded surface 9m of the guide connector 9 compresses the inner wall surface of the frame portion 20b of the disc valve 20 to be brought into close contact with the inner wall surface of the connector cover 16, it is prevented that the blood of the living body leaks from the disc valve 20 to the proximal end side in the outer needle unit 12.

Figure 9:
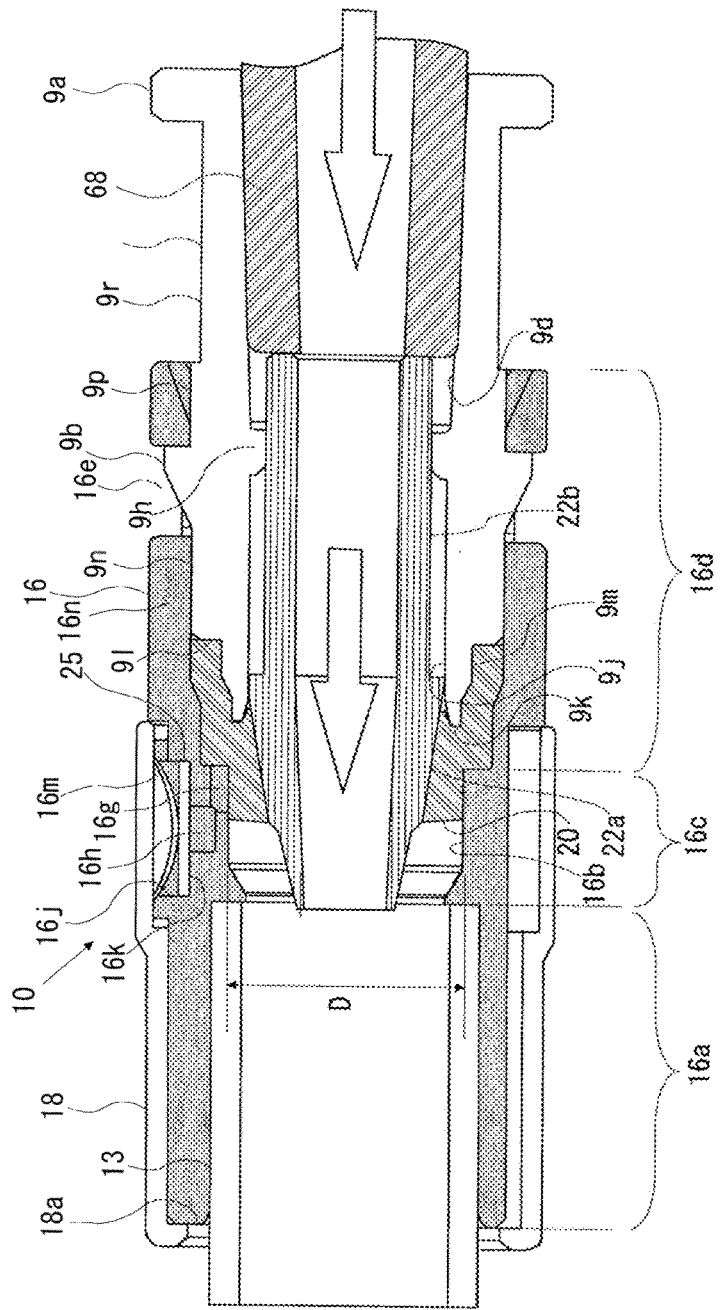
FIG. 9 is a cross-sectional view illustrating an example of the operation of the hub assembly according to the first embodiment of the invention.

Then, the user inserts the distal end portion of a connector 68 from the proximal end side of the guide connector 9 (or the outer needle unit 12) as illustrated in FIG. 9 to be taper-engaged and connected to the opening of the proximal end side of the guide connector 9. Alternatively, when a luer lock connector is adopted as the male connector, it is screwed and connected to the lock portion 9a. Along with this, the pusher 22 is pushed toward the distal end side in the axial direction by the distal end portion of the connector 68, and the distal end of the pusher 22 is pushed into the slit 20c of the disc valve 20. As a result, the portion around the slit 20c of the disc portion 20a of the disc valve 20 is elastically deformed toward the distal end side in the axial direction, the slit 20c is opened, and the proximal end side and the distal end side of the disc valve 20 communicate with each other. As a result, a passage is formed from the inner region of the connector 68 to the inside of the outer needle unit 12 and into the blood vessel of the living body, and infusion, blood transfusion, blood collection, etc. are performed.

When the pusher 22 is pushed toward the distal end side in the axial direction, the proximal end portion of the tapered portion 22a having the maximum diameter of the pusher 22 abuts on an inner wall surface 9j of the guide connector 9 with zero touch or is spaced with a slight distance. Therefore, the pusher 22 moves along the inner wall surface of the guide connector 9 and is pushed into the disc valve 20 on the distal end side in the axial direction. Alternatively, the pusher 22 is pushed into the disc valve 20 with a slight inclination angle even if it is inclined with respect to the axial direction.

Further, at that time, when the pusher 22 is pushed into the disc valve 20, the disc portion 20a of the disc valve 20 is deformed to the communication hole 16b side and closes the ventilation groove 16g. This is because the ventilation groove 16g is provided in a region reached by a part of the partition wall. Specifically, the ventilation groove 16g is provided within a predetermined distance in the axial direction from the distal end of the partition wall (the length from the outer peripheral edge of the deformation region of the disc portion 20a deformed by the pusher to the central portion of the slit 20c). As a result, it is prevented that the liquid medicine or blood introduced from the connector 68 flows into the ventilation groove 16g and the ventilation hole 16h due to the infusion or blood transfusion, and the inflow pressure of the liquid medicine or blood from the external device directly acts on the filter 25. Thus, in this embodiment, when the pusher 22 is pushed into the disc valve 20, the disc valve 20 closes the ventilation groove 16g, so that the load of the filter 25, for example, the action of the pump pressure of the external device can be reduced, the reliability such as durability of the apparatus can be improved, and the specifications of pressure resistance and welding of the filter 25 itself can be relaxed.

Further, the ventilation groove 16g is preferably located as close to the partition wall as possible, and is preferably adjacent to the partition wall. In this embodiment, the outer peripheral side of the deformation region of the disc portion 20a (the portion without the slit) closes the ventilation groove 16g. The portion of the disc portion 20a surrounded by the slit 20c may close the ventilation groove 16g entirely, but it is preferred that the outer peripheral side of the deformation region of the disc portion 20a (the portion without the slit) closes the ventilation groove 16g as much as possible. In this embodiment, the ventilation groove 16g is provided at the above-mentioned position, but the position of the ventilation groove 16g can be changed depending on the shape of the slit, the length of the slit, and the size of the pusher. Therefore, the ventilation groove 16g may be located in a region reached by a part of the disc valve 20 in which the portion around the slit 20c is deformed.

Then, after treatment or inspection, or at the time of interruption, the connector 68 is pulled out from the proximal end side of the guide connector 9 (or the outer needle unit 12), whereby the disc valve 20 is restored and deformed to the initial shape, and the pusher 22 is pushed back to the proximal end side by this elastic restoration. The movement of the pusher 22 toward the proximal end side is restricted by restoring the disc valve 20 to the assembled state or by bringing the proximal end portion of the tapered portion 22a of the pusher 22 into contact with the step portion 9h of the guide connector 9.

Here, in general, from the viewpoint of the flow rate required for the hub assembly 10 for performing infusion, blood collection, dialysis, etc., it is desirable that the inner wall surface 22b of the pusher 22 has a diameter of about φ1.5 mm or more. In that case, in order to close the ventilation groove 16g by the disc valve 20 deformed as described above, it is preferable that the diameter D of the communication hole 16b be φ3 mm or more in consideration of the deformation space of the disc valve 20. Therefore, in this embodiment, it is desirable that the diameter D of the communication hole 16b be φ3 mm or more. Further, it is desirable that a large diameter portion be provided in a part of the outer surface of the pusher 22 so that the large diameter portion of the pusher 22 pushes the outer peripheral side of the disc valve 20 in a circumferential shape.

Second Embodiment

Next, a second embodiment of the invention will be described. In this embodiment, an example will be described in which the opening from the liquid flow path in the hub assembly to the flow path of the ventilation path connected to the filter is opened at the distal end side as compared with the first embodiment. In the first embodiment, in the communication hole 16b, the ventilation groove 16g, which is a ventilation path for air or blood to the filter 25, is opened immediately before the distal end surface of the disc valve 20. This is to more reliably close the ventilation groove 16g when the pusher 22 pushes open the slit 20c of the disc valve 20.

Figure 10A:
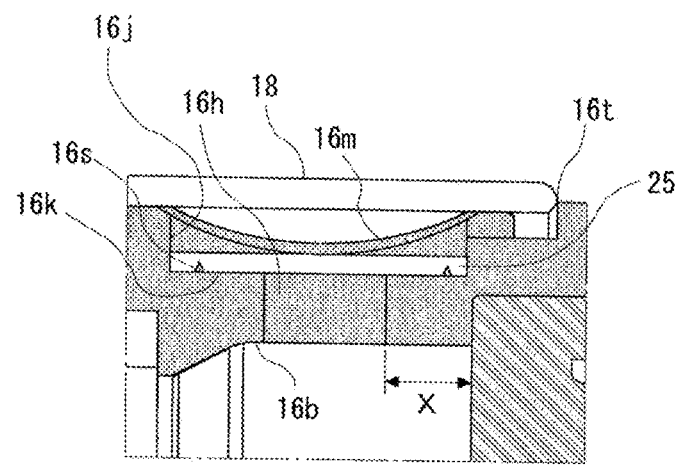
FIG. 10A and FIG. 10B are diagrams illustrating the vicinity of a filter in a hub assembly according to a second embodiment of the invention.
Figure 10B:
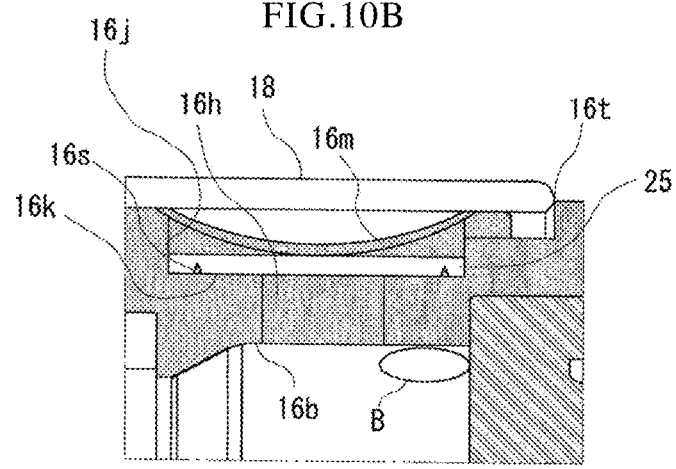

However, when the pusher 22 pushes and opens the slit 20c of the disc valve 20, it is not always necessary to completely close the ventilation groove 16g by the disc valve 20. Further, the ventilation groove 16g may be surrounded without directly contacting the ventilation groove 16g. Further, if the deformed disc valve 20 contacts a part of the rear end side of the opening of the ventilation groove 16g, the load on the filter 25 can be reduced to some extent. When considered in this way, the position of the opening of the ventilation path to the filter 25 may be closer to the distal end side. That is, in this case, it is not always necessary to provide the ventilation groove 16g, and as illustrated in FIG. 10A, the ventilation hole 16h may penetrate from the filter installation surface 16k to the communication hole 16b.

However, in that case, it is desirable that the position of the end portion of the opening of the ventilation hole 16h to the communication hole 16b on the disc valve 20 side is 10 mm or less (X≤10 mm) from the position of the distal end surface of the disc valve 20. According to this configuration, for example, when there is an air bubble B larger than 10 mm on the front side of the distal end surface of the disc valve 20, it is more reliably discharged from the ventilation hole 16h to the outside through the filter 25. Therefore, it is possible to prevent the air bubble B larger than 10 mm from flowing into the living body. Even if the air bubble B having a size of less than 10 mm flows into the living body, it is unlikely that the health is adversely affected, and it is possible to ensure the safety of the hub assembly according to this embodiment. In this embodiment, the position of the end of the opening of the ventilation hole 16h to the communication hole 16b on the disc valve 20 side is 10 mm or less from the position of the distal end surface of the disc valve 20, but it is more preferable that the position of the end portion on the distal end side in the opening of the ventilation hole 16h to the communication hole 16b be 10 mm or less from the position of the distal end surface of the disc valve 20. According to this configuration, the entire opening of the ventilation hole 16h to the communication hole 16b can be set to 10 mm or less from the position of the distal end surface of the disc valve 20. As a result, it is possible to more reliably prevent large air bubbles B from flowing into the living body.

Although the embodiments of the invention have been described in detail above, the invention is not limited by the specific description thereof, and is carried out in a mode in which various changes, modifications, and improvements are added based on the knowledge of those skilled in the art. Further, such embodiments are also included in the scope of the invention without departing from the spirit of the invention.

For example, in the above embodiment, the guide connector 9 which is an example of the hub body has been inserted into the connector cover 16 which is an example of the hub exterior body, and the disc valve 20 has been sandwiched and fixed between the both. The hub may be formed by integrally forming the connector cover 16 and the guide connector 9. In this case, a fixing member may be separately inserted into the hub in order to fix the disc valve 20.

Further, in the above embodiment, as the filter 25, a disc-shaped membrane filter has been used, but instead of this, a ring-shaped filter (for example, a sponge filter, a porous filter) may be configured to surround the entire circumference of the outer wall surface of the connector cover 16. Further, in the above embodiment, the filter 25 has been disposed on the distal end side of the disc valve 20, that is, on the living body side, and the entire ventilation path from the liquid flow path in the hub assembly to the outside of the connector cover 16 through the filter has been disposed on the distal end side of the disc valve 20. However, in the invention, the filter 25 and the opening of the ventilation path to the outside of the connector cover 16 may be present on the rear end side of the disc valve 20, that is, on the external device side. The ventilation path may partially contact the outer peripheral surface of the partition wall.

Further, for example, in the above embodiment, the outer needle 14, the outer needle base 14a, and the clamping tube 13 have been fixed to the distal end of the hub assembly 10, and the inner needle unit (not illustrated) has been inserted to the outer needle unit 12 to form the indwelling needle assembly. However, a catheter or the like may be fixed to the distal end of the hub assembly 10 and the inner needle unit may be inserted to form the indwelling catheter assembly or the like. The effects of the invention can be similarly exerted in such an indwelling catheter assembly.

Further, the materials of the connector cover 16, the disc valve 20, the pusher 22, the filter 25, the guide connector 9, and the filter cap 18 can be appropriately changed according to the purpose and specifications. Further, for example, the method of connecting the connector cover 16 and the guide connector 9 may be another method. More specifically, ultrasonic welding or a screwing method may be adopted. Further, the material of the filter cap 18 does not necessarily need to be transparent, and the filter cap 18 may be formed using an opaque material, or may have a color having a specific meaning.

Third Embodiment

<Basic Configuration>

Figure 11A:
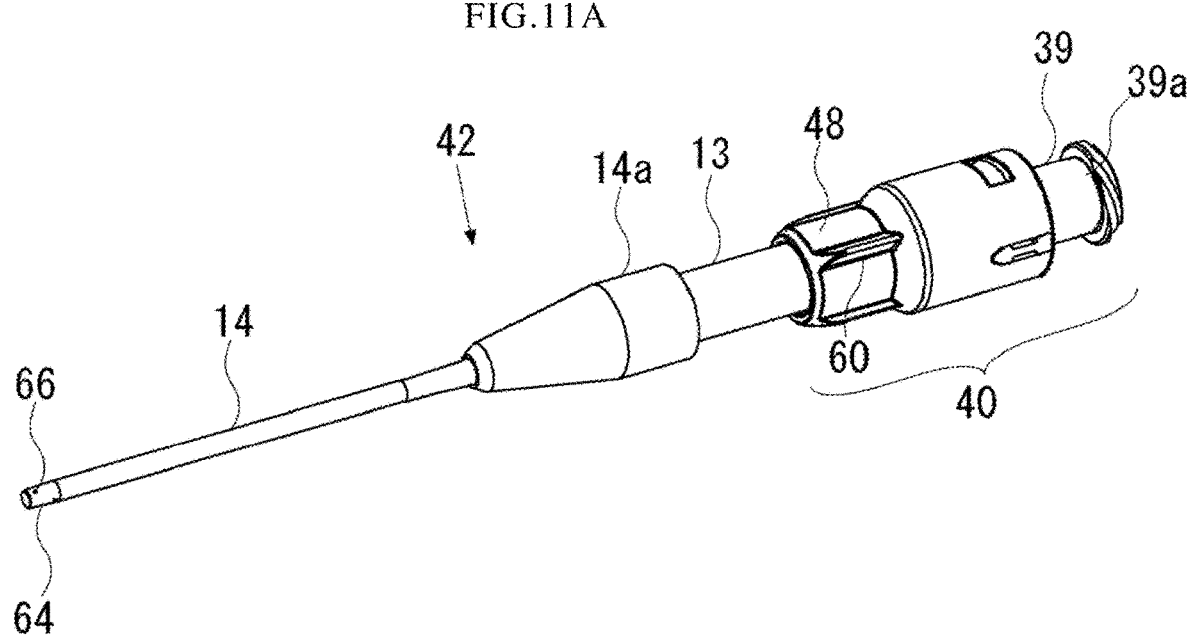
FIG. 11A and FIG. 11B are perspective views of an outer needle unit in a third embodiment of the invention.
Figure 11B:
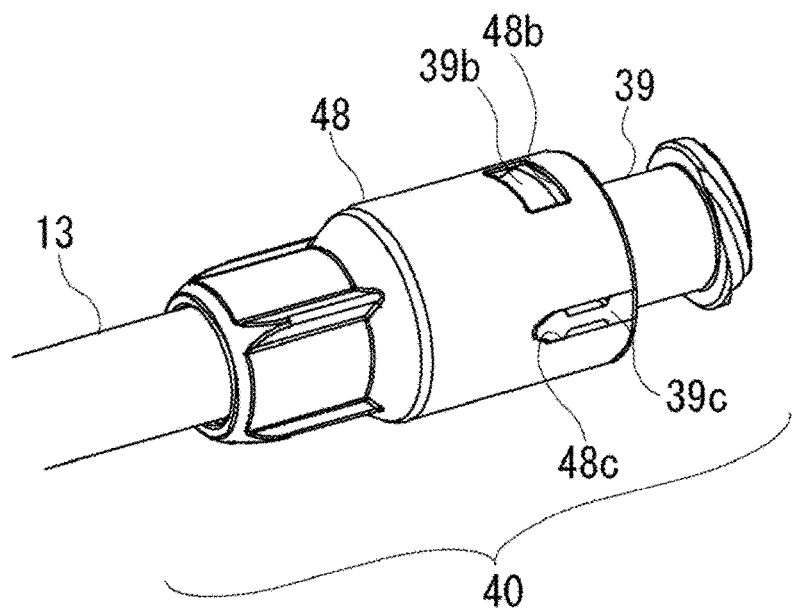
Figure 12:
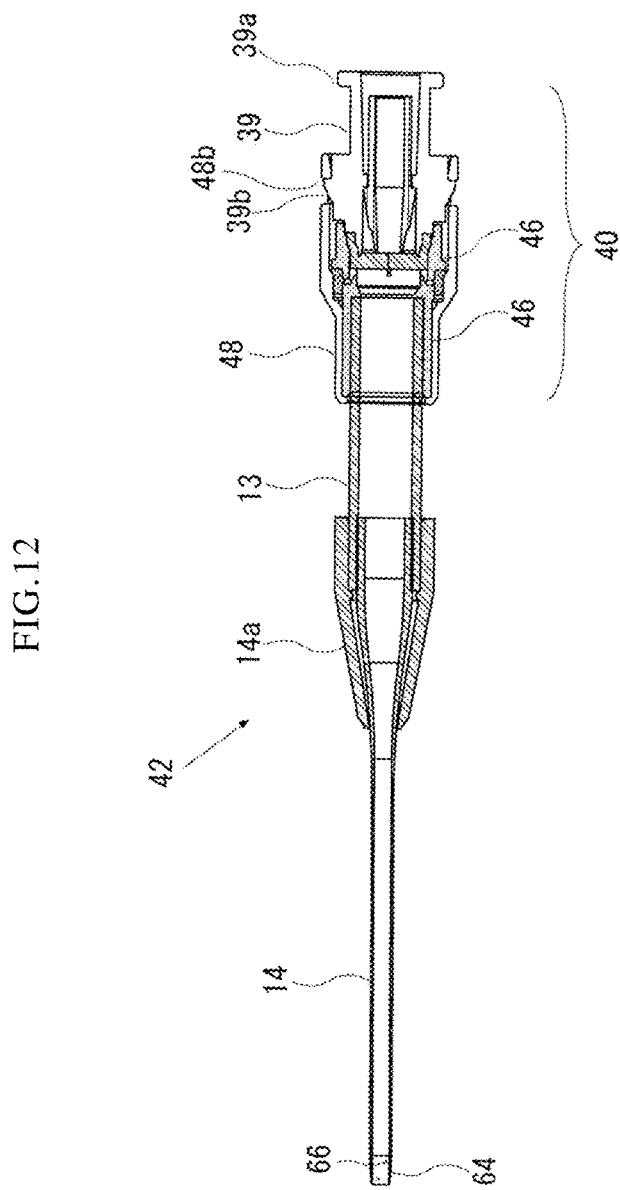
FIG. 12 is a cross-sectional view of the outer needle unit according to the third embodiment of the invention as seen from a direction perpendicular to an axis.

FIGS. 11 and 12 illustrate an outer needle unit 42 in an indwelling needle assembly including a hub assembly 40 as a third embodiment of the invention. FIG. 11A is a perspective view of the outer needle unit 42, and FIG. 11B is an enlarged view of a perspective view of the hub assembly 40 in particular. FIG. 12 is a cross-sectional view of the outer needle unit 42 as seen from a direction perpendicular to the axial direction. The cylindrical clamping tube 13, the outer needle 14, and the outer needle base 14a in the outer needle unit 42 illustrated in FIG. 11 are the same as those described in the first embodiment, and therefore the description thereof is omitted here.

As illustrated in FIG. 12, a schematic shape of the hub assembly 40 is formed by inserting a guide connector 39 which is an example of a hub body into a proximal end side of a connector cover 46 which is an example of a hub exterior body. The connector cover 46 has a substantially cylindrical shape. Similar to the first embodiment, a lock portion 39a provided with a screw thread is formed on the outer wall surface of the proximal end side opening of the guide connector 39. Further, in this embodiment, a filter cap 48 is attached so as to fix the connector cover 46 and the guide connector 39. Further, on the outer wall surface of the filter cap 48 on the distal end side, a plurality of ridges 60 are formed in parallel with the axial direction so that the user can easily grasp.

Figure 13:
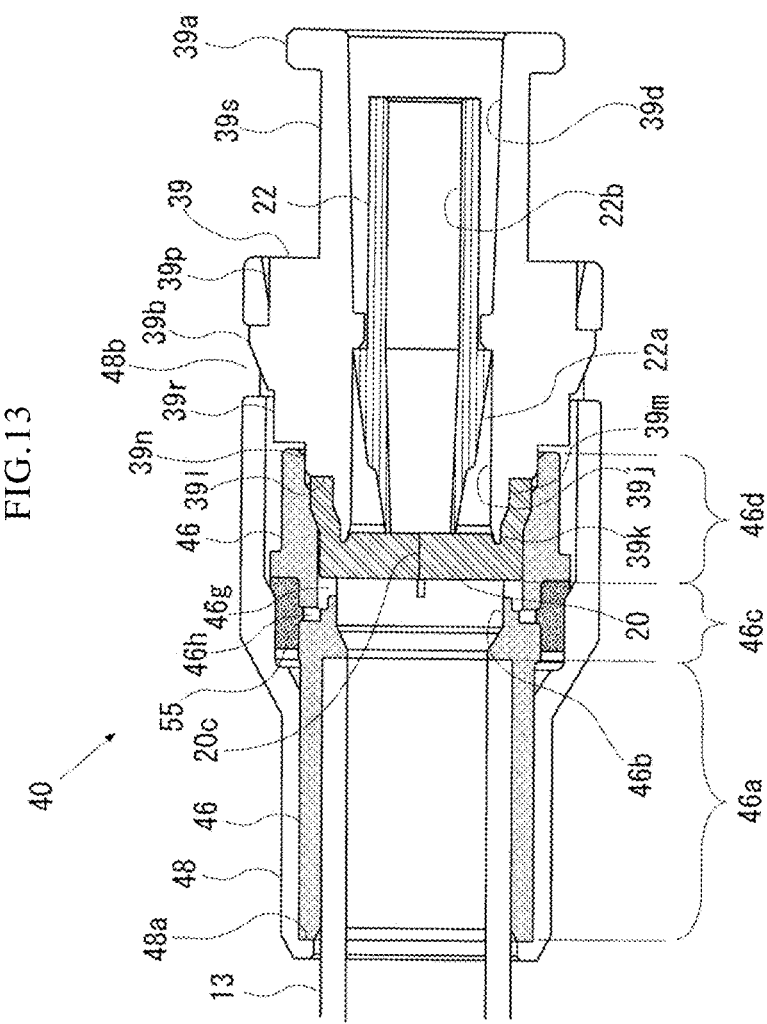
FIG. 13 is a cross-sectional view of a hub assembly according to the third embodiment of the invention as seen from a direction perpendicular to an axis.

Next, the structure of the hub assembly 40 will be described in more detail with reference to FIG. 13. FIG. 13 is a cross-sectional view of the hub assembly 40 as seen from a direction perpendicular to the axial direction. Inside the connector cover 46, a distal-end fitting portion 46a into which the clamping tube 13 is fitted is provided on the distal end side, a proximal-end insertion portion 46d into which the guide connector 39 is inserted and fixed is provided at the proximal end side, and a connection wall portion 46c forming a communication hole 46b is provided between the distal-end fitting portion 46a and the proximal-end insertion portion 46d.

As described above, the clamping tube 13 is press-fitted and fixed to the distal-end fitting portion 46a from the distal end side. Further, the disc valve 20 and the guide connector 39 are inserted into the proximal-end insertion portion 46d. Further, the outer diameter and the inner diameter of the filter cap 48 are reduced at its distal end, and a step 48a provided in the inner wall at the distal end of the reduced diameter is brought into contact with the distal end of the connector cover 46 to restrict the movement toward the distal end side of the connector cover 46.

Returning to FIG. 11B, a cap position restricting claw 39b provided in the guide connector 39 engages with a cap engaging hole 48b of the filter cap 48, so that the filter cap 48, the connector cover 46, and the guide connector 39 are combined. Further, a cap position restricting convex portion 39c provided in the guide connector 39 engages with a cap engagement slit 48c of the filter cap 48, so that movement of the guide connector 39 toward the distal end side of the filter cap 48 or rotation around the axis is restricted.

As can be seen from FIG. 13, in this embodiment, the disc valve 20 equivalent to that described in the first embodiment is sandwiched and fixed between a distal end portion 39k of the guide connector 39 inserted into the connector cover 46 and the wall surface of the connector cover 46 on the proximal end side in the connection wall portion 46c. That is, in this embodiment, the position of the guide connector 39 in the axial direction with respect to the connector cover 46 can be changed by the elasticity of the disc valve 20. The position of the distal end of the connector cover 46 is restricted by the step 48a of the filter cap 48, and the position of the proximal end side of the cap position restricting claw 39b of the guide connector 39 is restricted by the cap engaging hole 48b of the filter cap 48. As a result, the positions of the connector cover 46 and the guide connector 39 in the axial direction are determined.

Further, in this embodiment, unlike the planar filter 25 (planar filtering structure such as a membrane filter) illustrated in the first embodiment, a three-dimensional filter 55 having a ring shape (three-dimensional filtering structure) is held in a state of being radially compressed and sandwiched between the outer wall surface of the connector cover 46 and the inner wall surface of the filter cap 48. Liquid-tightness and pressure resistance can be suitably improved by compressing the three-dimensional filtering structure so as to be orthogonal to the fluid passage direction or to have an angle with the fluid passage direction. It is possible to reduce that blood leaks to the outside. Further, the three-dimensional filter 55 (three-dimensional filtering structure) can be easily manufactured as a hub assembly by forming at least a part of the ring shape. For example, the three-dimensional filter 55 may have a tubular shape long in the axial direction. The shape of the three-dimensional filtering structure can be appropriately changed regardless of the ring shape, but in any case, it is preferable that the filtering structure is compressed by an adjacent member.

The filter 55 is a hydrophobic filter. For example, the three-dimensional filtering structure may be one obtained by heating and sintering a resin powder such as polyethylene or polypropylene (sintered body). Since the hydrophobic filter reduces or loses air permeability when it comes into contact with liquid, it is possible to prevent the air from entering the hub body from the outside through the ventilation path after the hub body is filled with the liquid. Further, the filter 55 may be made of a porous material. Further, it is preferable to disperse in the filter 55a polymer or the like that swells by absorbing a liquid such as blood and closes the flow path of the liquid or gas in the filter 55. More specifically, this polymer may be a so-called superabsorbent polymer. In this case, the gap of the filter is filled with the polymer or the like and the flow path of the fluid is closed, so that the pressure resistance can be improved. The pressure resistance of the filter 55 in this case is preferably 200 mmhg or more. Alternatively, considering that the average arterial pressure of a dialysis patient is 120 to 140 mmhg, the pressure resistance of the filter 55 is preferably 120 mmhg or more. Further, it may be considered that the object of use is a child, and in that case, lower pressure resistance may be used.

The filter 55 does not necessarily have to be held in a state of being radially compressed and sandwiched between the outer wall surface of the connector cover 46 and the inner wall surface of the filter cap 48. For example, the inner diameter of the filter 55 is formed to be slightly smaller than the outer diameter of the connector cover 46, and when the filter 55 is fitted into the connector cover 46, the inner wall of the filter 55 is expanded by the connector cover 46, and thus may be substantially compressed in the radial direction. Further, in the axial direction of the hub assembly 40, the hard member (hub distal end side member), the filter 55, the hard member (hub proximal end side member) may be arranged in series, and the filter 55 may be compressed in the axial direction with the two hard members, the hub distal end side member and the hub proximal end side member.

Figure 14:
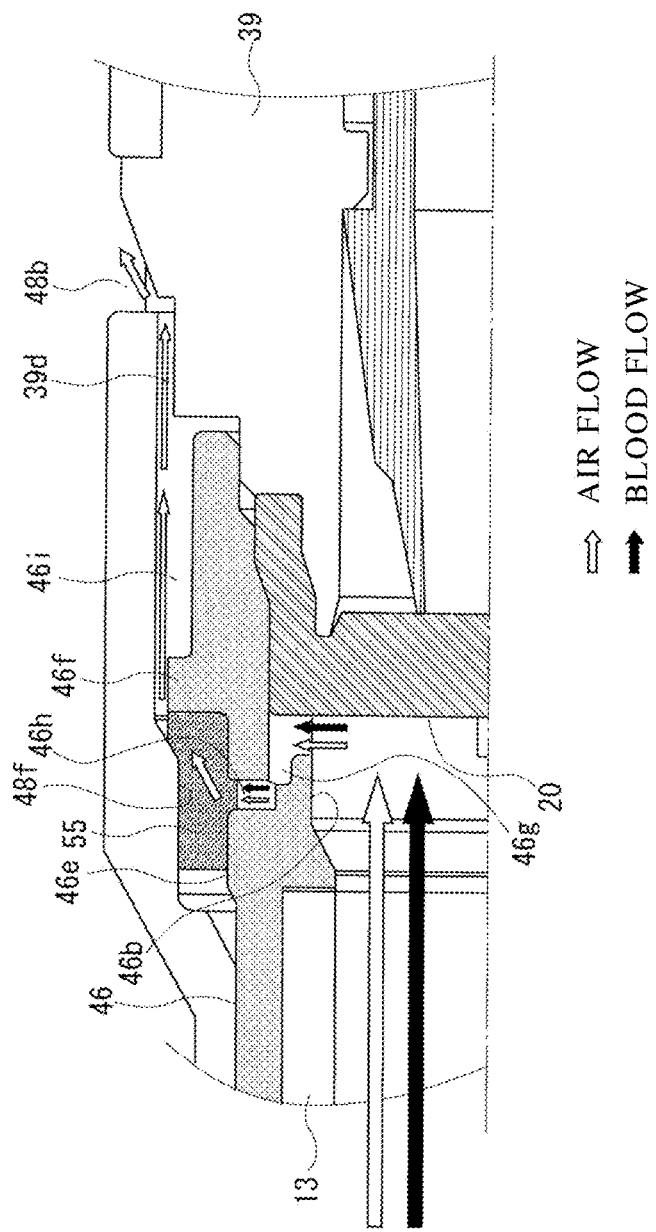
FIG. 14 is a diagram illustrating the vicinity of a filter in the hub assembly according to the third embodiment of the invention.

FIG. 14 illustrates an enlarged view of the vicinity of the filter 55 in the hub assembly 40. As illustrated in FIGS. 13 and 14, the outer wall of the connector cover 46 is provided with a filter restricting portion 46f protruding to the outer peripheral side. When the filter 55 is fitted from the distal end side to a filter fitting portion 46e in the outer wall surface of the substantially cylindrical connector cover 46, the filter restricting portion 46f comes into contact with the end surface on the proximal end side of the filter 55. Thus, the filter 55 is prevented from excessively moving toward the proximal end side of the connector cover 46.

Further, in the inner wall of the filter cap 48, there is provided a filter compressing portion 48f, which is a part having reduced diameter from the proximal end side of the filter cap 48, in a portion facing the filter fitting portion 46e in the state where the distal end of the connector cover 46 is in contact with the step 48a of the filter cap 48. The filter compressing portion 48f, together with the filter fitting portion 46e of the connector cover 46, radially compresses and fixes the filter 55.

The filter fitting portion 46e of the connector cover 46 is provided with a ventilation hole 46h which is a concave hole formed from the outer wall surface of the connector cover 46 toward the inner peripheral side. The ventilation holes 46h are provided in four places at every 90 degrees when viewed from the axial direction. On the other hand, the inner wall surface of the communication hole 46b in the connector cover 46 is provided with a ventilation groove 46g for allowing the air in the communication hole 46b to escape to the outside. The ventilation grooves 46g are recessed grooves that are provided in four places on the inner wall surface of the communication hole 46b at positions corresponding to the ventilation holes 46h at every 90 degrees when viewed from the axial direction, and extend in the front-rear direction. As illustrated in FIG. 14, the cross-sectional shape of the ventilation groove 46g when viewed from the circumferential direction is an inverted L-shape such that the outer peripheral side extends toward the distal end side rather than the inner peripheral side. A part of the ventilation groove 46g on the outer peripheral side communicates with the ventilation hole 46h.

Therefore, the air in the communication hole 46b passes through the filter 55 through the ventilation groove 46g and the ventilation hole 46h. Further, the air can flow out from the cap engaging hole 48b to the outside through a ventilation path 46i which is a gap between the inner wall surface of the filter cap 48 and the outer wall surface of the connector cover 46, and a ventilation path 39d which is a gap between the inner wall surface of the filter cap 48 and the outer wall surface of the guide connector 39.

On the other hand, the liquid such as blood existing in the communication hole 46b reaches the filter 55 through the ventilation groove 46g and the ventilation hole 46h, but is blocked by the filter 55 and prevented from leaking to the outside. In this embodiment, the ventilation path 46i formed by the gap between the inner wall surface of the filter cap 48 and the outer wall surface of the connector cover 46, and the ventilation path 39d formed by the gap between the inner wall surface of the filter cap 48 and the outer wall surface of the guide connector 39 are examples of the cap ventilation part. Further, as another example of the cap ventilation part, ventilation may be performed by providing a through hole in the filter cap 48.

Further, in this embodiment, the positions of the ventilation groove 46g and the ventilation hole 46h in the axial direction are deviated. By doing so, the ventilation groove 46g can be adjacent to the disc valve 20 as a partition wall while simplifying the structure of the mold at the time of molding the connector cover 46. Further, since a ventilation path with a small flow path is formed between the filter 55 and the ventilation opening (the ventilation groove 46g), it is difficult for the liquid existing in the communication hole 46b to come into contact with the filter 55, and the air in the communication hole 46b can be smoothly exhausted. However, the positions of the ventilation groove 46g and the ventilation hole 46h may be matched. Further, the substantially cylindrical pusher 22 is disposed on the proximal end side of the disc valve 20 in this embodiment as in the first embodiment, but the detailed description thereof will be omitted here. Further, in this embodiment, as described above, the cross-sectional shape of the ventilation groove 46g as viewed from the circumferential direction is an inverted L-shape such that the outer peripheral side extends toward the distal end side rather than the inner peripheral side. As a result, the opening of the ventilation groove 46g to the communication hole 46b can be brought closer to the disc valve 20. As a result, when the pusher is inserted into the disc valve 20 and the disc portion 20a of the disc valve 20 is deformed toward the distal end side, it is possible to more reliably close the opening of the ventilation groove 46g to the communication hole 46b.

Figure 15:
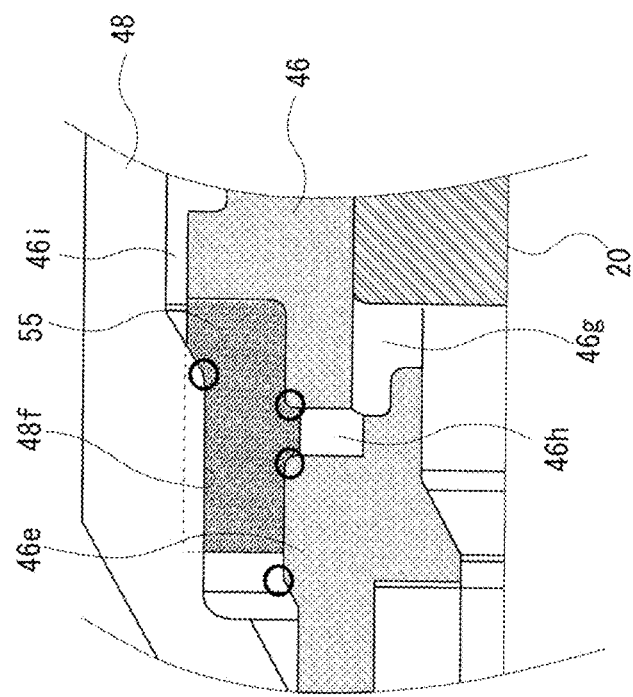
FIG. 15 is an enlarged view illustrating the vicinity of the filter in the hub assembly according to the third embodiment of the invention.

FIG. 15 illustrates a further enlarged view of the configuration around the filter 55 in this embodiment. As illustrated in FIG. 15, in this embodiment, in the filter fitting portion 46e of the connector cover 46, the corner portions (edge portions) where the filter 55 may come into contact when the filter 55 is fitted are subjected to R. More specifically, as illustrated by a circle in FIG. 15, R is provided in the edge portion of a tapered inclined surface in which the diameter of the filter fitting portion 46e increases from a portion on the more distal end side of the connector cover 46, and the edge portion of the opening of the ventilation hole 46h in the filter fitting portion 46e.

The size of this R may be 0.05 mm to 1.0 mm. Thereby, when fitting the filter 55 from the front distal end side of the connector cover 46, it is possible to suppress the inconvenience that the edge of the outer wall surface of the connector cover 46 scrapes the filter 55.

Similarly, as illustrated in FIG. 15, in this embodiment, in the filter compressing portion 48f of the filter cap 48, R is applied also to the edge portion of the tapered inclined surface whose diameter is reduced from the portion closer to the proximal end side of the inner wall of the filter cap 48. The size of this R may also be 0.05 mm to 1.0 mm. Thereby, when the filter 55 is fitted to the connector cover 46, and these are fitted into the filter cap 48, it is possible to suppress the inconvenience that the edge of the inner peripheral surface of the filter cap 48 scrapes the filter 55.

Figure 16A:
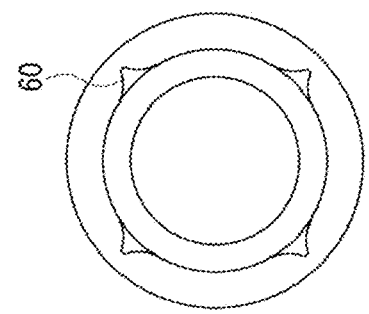
FIG. 16A and FIG. 16B are schematic diagrams of a filter cap in the third embodiment of the invention.
Figure 16B:
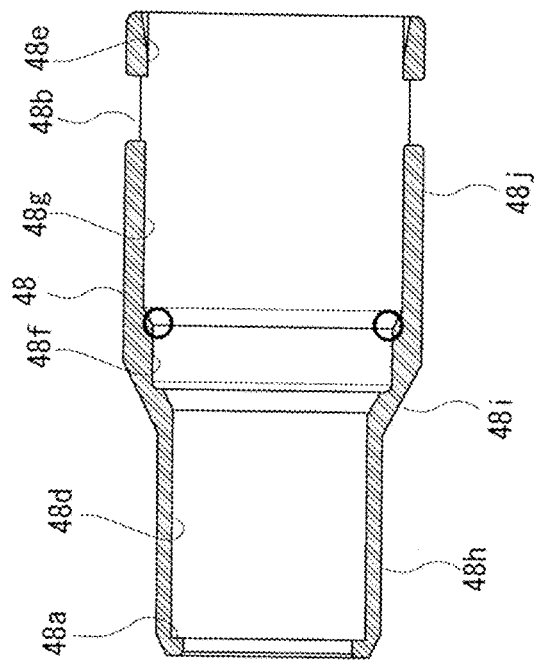

FIG. 16 illustrates a schematic diagram of the filter cap 48 in this embodiment. FIG. 16A is a view as seen from the front in the axial direction, and FIG. 16B is a cross-sectional view as seen from a direction perpendicular to the axial direction. As can be seen from FIG. 16B, the filter cap 48 is a substantially cylindrical member, and a proximal end side portion 48j is formed by expanding the diameter from a distal end side portion 48h via a tapered portion 48i. As can be seen from FIG. 16A, there are provided four ridges 60 at every 90 degrees on the outer peripheral surface of the distal end side portion 48h.

As can be seen from FIG. 16B, the step 48a is provided in the inner peripheral surface of the distal end. Further, an inner peripheral surface 48d of the distal end side portion 48h has a diameter substantially the same as or slightly larger than the outer diameter of the distal-end fitting portion 46a of the connector cover 46. When the connector cover 46 is inserted into the filter cap 48, there is established a dimensional relationship such that no large rattling occurs. Then, the inner wall surface of the proximal end side portion 48j, which is located further to the proximal end side of the filter compressing portion 48f in the filter cap 48, is a ventilation path forming portion 48g in which the diameter of the filter compressing portion 48f is further expanded. The ventilation path forming portion 48g forms the ventilation path 46*i* and the ventilation path 39*d* together with the connector cover 46 and the outer wall surface of the guide connector 39.

The position of the filter 55 inside the filter cap 48 is determined when the filter 55 is inserted in contact with the filter fitting portion 46*e* of the connector cover 46 and the filter restricting portion 46*f*, and the distal end of the connector cover 46 is in contact with the step 48*a*. In this embodiment, in this state, the end surface of the filter compressing portion 48*f* on the distal end side is located further on the distal end side with respect to the end surface on the distal end side of the filter 55, and a gap is formed between the both (see FIGS. 13 to 15). As a result, the filter 55 is compressed between the filter compressing portion 48*f* of the filter cap 48 and the filter fitting portion 46*e* of the connector cover 46. Even if the filter 55 extends in the front-rear direction, it is prevented that the filter 55 comes into contact with the end surface of the filter compressing portion 48*f* on the distal end side, and the compression of the filter 55 is inhibited.

An inner wall surface 48*e* further on the proximal end side of the cap engaging hole 48*b* in the proximal end side portion 48*j* of the filter cap 48 has substantially the same diameter as the ventilation path forming portion 48*g*, has a diameter substantially the same as or slightly larger than that of a second cap insertion surface 39*p* (described later) in the guide connector 39, and restricts the radial position and inclination of the guide connector 39 inside the filter cap 48 when the guide connector 39 is inserted into the filter cap 48.

FIG. 17 illustrates a schematic diagram of the connector cover 46 in this embodiment. FIG. 17A is a view as seen from the front in the axial direction, and FIG. 17B is a cross-sectional view as seen from a direction perpendicular to the axial direction. The connector cover 46 is provided with a disc contact portion 46*k* with which the outer wall of the disc portion 20*a* of the disc valve 20 contacts and the position of the disc portion 20*a* in the direction perpendicular to the axis is restricted. The disc portion 20*a* of the disc valve 20 is compressed in the center direction by the disc contact portion 46*k*. This is to prevent the liquid from leaking from between the pusher 22 and the slit 20*c* when the pusher 22 is pushed into the slit 20*c* of the disc valve 20. Similarly, there are provided with a frame contact portion 46*m* to which the outer periphery of the frame portion 20*b* of the disc valve 20 abuts in the state expanded to the outer peripheral side by the guide connector 39, and a cover contact surface 46*n* that restricts the position and inclination in the radial direction of a cover insertion surface 39*n* (described later) of the guide connector 39. The diameters increases in the order of the disc contact portion 46*k*, the frame contact portion 46*m*, and the cover contact surface 46*n*.

FIG. 18 illustrates a schematic diagram of the guide connector 39. FIG. 18A is a view as seen from the front in the axial direction, and FIG. 18B is a cross-sectional view as seen from a direction perpendicular to the axial direction. The guide connector 39 is a substantially cylindrical member. At the installation position, the distal end portion 39*k* of the guide connector 39 enters the groove 20*d* of the disc valve 20 and presses the groove 20*d* against the wall surface of the connection wall portion 46*c* in the proximal-end insertion portion 46*d* of the connector cover 46, thereby restricting the position and orientation of the disc portion 20*a* in the axial direction.

Further, on the outer wall surface of the distal end portion 39*k* on the proximal end side, a diameter-expanded surface 39*m* that is expanded in a tapered shape in diameter is formed. The outer wall surface of the diameter-expanded surface 39*m* abuts on the inner wall surface of the frame portion 20*b* of the disc valve 20. Then, the frame portion 20*b* of the disc valve 20 is radially sandwiched between the frame contact portion 46*m* of the proximal-end insertion portion 46*d* of the connector cover 46 and the outer wall surface of the diameter-expanded surface 39*m* of the guide connector 39. With this configuration, the disc valve 20 is also supported. This ensures the air-tightness and the liquid-tightness between the outer wall surface of the disc valve 20 and the inner wall surface of the connector cover 46. Further, the outer wall surface of the diameter-expanded surface 39*m* may not only abut on the inner wall surface of the frame portion 20*b* of the disc valve 20, but may have such a dimensional relationship as to push the inner wall surface.

Further, a vertical surface 39*l* which is a wall surface vertically raised on the outer peripheral side is provided on the proximal end side of the diameter-expanded surface 39*m* of the guide connector 39. This vertical surface 39*l* presses the end portion of the frame portion 20*b* of the disc valve 20 on the proximal end side toward the distal end side when the guide connector 39 is assembled. Therefore, the frame portion 20*b* of the disc valve 20 is axially sandwiched between the wall surface of the connection wall portion 46*c* of the connector cover 46 and the vertical surface 39*l* of the guide connector 39, which more reliably supports the disc valve 20.

The guide connector 39 is inserted into the connector cover 46 and the filter cap 48, the cap position restricting claw 39*b* is engaged with the cap engaging hole 48*b* of the filter cap 48, and the cap position restricting convex portion 39*c* is engaged with the cap engagement slit 48*c* of the cap engaging slit of the filter cap 48, so that the positions of the connector cover 46 and the guide connector 39 inside the filter cap 48 are determined. In this embodiment, the cap position restricting convex portion 39*c* has a double arrow shape in which the central portion in the axial direction is thin, as viewed in the radial direction, as illustrated in FIG. 11B. This is a configuration for preventing the deterioration of the shape accuracy due to the shrinkage of the resin of the cap position restricting convex portion 39*c* at the time of molding.

Further, the cover insertion surface 39*n* facing the cover contact surface 46*n* of the connector cover 46 is provided on the proximal end side of the vertical surface 39*l* in the outer wall surface of the guide connector 39. The cover insertion surface 39*n* has an outer diameter to be substantially the same as or slightly smaller than the cover contact surface 46*n* of the connector cover 46, and can stabilize the position and inclination in the direction perpendicular to the axis of the guide connector 39 in the connector cover 46.

On the distal end side of the cap position restricting claw 39*b* in the outer wall surface of the guide connector 39, there is provided a first cap insertion surface 39*r* facing the ventilation path forming portion 48*g* which is the inner wall surface on the distal end side from the cap engaging hole 48*b* of the filter cap 48 so as to form the ventilation path 39*d* together with the ventilation path forming portion 48*g*. The second cap insertion surface 39*p* facing the inner wall surface on the proximal end side from the engagement hole 16*e* of the connector cover 16 is provided on the proximal end side of the cap position restricting claw 39*b* in the outer wall surface of the guide connector 39. The second cap insertion surface 39*p* has an outer diameter that is substantially the same as or slightly smaller than the inner wall surface 48*e* on the proximal end side of the cap engaging hole 48*b* in the filter cap 48, and helps the stabilization of the position and inclination in the direction perpendicular to the axis of the guide connector 39 in the filter cap 48.

An exposed surface 39s, which is a portion exposed to the proximal end side of the filter cap 48, is provided further on the proximal end side of the second cap insertion surface 39p on the outer wall surface of the guide connector 39. The outer wall surface of this exposed surface 39s has a diameter to be smaller than the first cap insertion surface 39r and the second cap insertion surface 39p, and ensures workability when connecting the connector at the distal end of the tube from an external device to the guide connector 39. In addition, in the state where the connector cover 46 and the guide connector 39 are assembled to the filter cap 48, the exposed surface 39s of the guide connector 39 is in the form of an annular depression. Therefore, the device can be made compact as a whole, and even when the connector is connected to the skin and fixed, it is easy to make the entire body substantially parallel to the skin, and the number of corners and the like that cause pain on the skin of the patient can be reduced.

Further, the filter cap 48, the connector cover 46, and the guide connector 39 described above may be formed of a material having rigidity that allows the initial shape to be maintained without being substantially deformed by an external force that acts. Preferably, a hard synthetic resin material may be employed. For example, polycarbonate, polyamide, polysulfone, polyarylate, or the like may be used. Further, the material forming the guide connector 39 may be lower in hardness than the material forming the connector cover 46 and the filter cap 48. By doing so, it is possible to suppress the galling between the guide connector 39 and the connector from the external device while ensuring the strength of the entire hub assembly.

Figure 20:
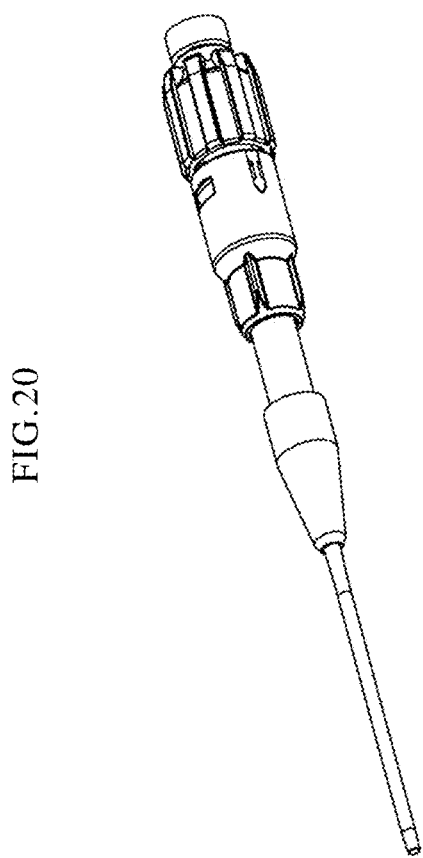
FIG. 20 is a perspective view illustrating a state in which a connector is attached to the outer needle unit according to the third embodiment of the invention.

FIG. 19 illustrates a schematic diagram of the indwelling needle assembly with the connector 68 attached. FIG. 19A is a side view and a view as seen from the axial rear surface, and FIG. 19B is a cross-sectional view taken along the line A-A. By rotating a lock screw part 68a with respect to the connector 68, a screw part 68b formed on the inner wall of the lock screw part 68a is screwed to the lock portion 39a of the guide connector 39, so that the connector 68 is fixed to the guide connector 39. FIG. 20 illustrates a perspective view of the indwelling needle assembly with the connector 68 attached.

<Operations>

When using the indwelling needle assembly including the hub assembly 40 having the above-described structure, first, the indwelling needle assembly is punctured into a blood vessel of a living body, and then the inner needle unit described in the first embodiment is pulled out from the outer needle unit 42 to the proximal end side. As a result, the outer needle unit 42 is left in the state of being punctured by the blood vessel of the patient. At that time, the inner needle is removed from the disc valve 20, whereby the disc valve 20 is restored to the initial shape, and the slit 20c is closed.

At this time, for example, the air existing in the clamping tube 13 is pushed out toward the proximal end side by the inflow pressure of blood. This air flows into the ventilation groove 46g provided in the inner wall surface of the connector cover 46. Then, the air further flows into the ventilation hole 46h and reaches the filter 55. Since the filter 55 is configured to be able to pass air (gas), the air passes through the ventilation path 46i and the ventilation path 39d as it is and is discharged to the outside from the cap engaging hole 48b. As a result, the air can flow out from the inside of the clamping tube 13 to the outside through the communication hole 46b, the ventilation groove 46g, the ventilation hole 46h, the filter 55, the ventilation path 46i, and the ventilation path 39d.

As a result, the outer needle 14 and the clamping tube 13 are filled with blood. By visually recognizing the "flashback", the user can confirm that the outer needle unit 42 is normally punctured into the blood vessel of the living body. In addition, in this embodiment, the ventilation grooves 46g and the ventilation holes 46h are provided at four positions at every 90 degrees in the circumferential direction in the inner wall of the connector cover 46. Therefore, even if the indwelling needle assembly including the hub assembly 40 is inclined, the air can flow out to the outside through the ventilation groove 46g and the ventilation hole 46h at any one of the four locations. The air is easy to exhaust, and it is possible to cause "flashback" more reliably.

When the inner needle comes off from the disc valve 20, the blood fills the clamping tube 13 and a part of the blood flows into the communication hole 46b, the ventilation groove 46g, and the ventilation hole 46h, but is disturbed from flowing out to the outside by the filter 55. Further, since the diameter-expanded surface 39m of the guide connector 39 compresses the inner wall surface of the frame portion 20b of the disc valve 20 to be brought into close contact with the frame contact portion 46m of the connector cover 46, it is prevented that the blood of the living body leaks from the disc valve 20 to the proximal end side in the outer needle unit 12.

Further, at that time, when the pusher 22 is pushed into the disc valve 20, the disc portion 20a of the disc valve 20 is deformed to the communication hole 46b side and closes the ventilation groove 46g. This is because the ventilation groove 46g is provided in a region reached by a part of the disc portion 20a. Specifically, the ventilation groove 46g is provided within a predetermined distance in the axial direction from the distal end of the partition wall (the length from the outer peripheral edge of the deformation region of the disc portion 20a deformed by the pusher to the central portion of the slit 20c). As a result, regardless of the position of the slit or the like, it is prevented that the liquid medicine or blood introduced from the connector 68 flows into the ventilation groove 46g and the ventilation hole 46h due to the infusion or blood transfusion, and the inflow pressure of the liquid medicine or blood from the external device directly acts on the filter 55.

Further, as an example of an assembly procedure of the hub assembly 40 in this embodiment, the following procedure is considered.

(1) The filter 55 is fitted to the connector cover 46. (2) The filter 55 is fitted to the connector cover 46 and inserted together into the filter cap 48 to form a first unit. (3) The pusher 22 is stored in the guide connector 39, and the disc valve 20 is attached from the distal end side to form a second unit. (4) The second unit is inserted from the proximal end side of the first unit. However, the procedure for assembling the hub assembly in this embodiment is not limited to the above. Further, in this embodiment, the disc valve 20 includes the frame portion 20b extending toward the proximal end side, and is fixed by the distal end of the internally inserted guide connector 39 and the externally inserted connector cover 46, but the disc valve 20 may be fixed by a separate member. Further, the disc valve 20 may be shaped to have a frame portion extending toward the distal end side, and may be fixed by an internally inserted connector cover and an externally inserted guide connector, or may be fixed by a separate member.

In addition, in the above-described embodiment, a member formed of one member may be divided into a plurality of members according to their functions. For example, the distal end portion (portion for fixing the disc valve) of the guide connector may be a separate member to form a plurality of members. Further, a member for fixing the disc valve may be separately provided inside the guide connector, and in this case, the connector cover and the guide connector may be one member. Further, the filter cap and the connector cover may be the same member, or may be formed as one member by welding each member.

Further, in the above embodiment, it is preferable that the disc valve, which is a partition wall, has the flow path opened by inserting the lure into the hub assembly. As an example other than the disc valve of the type described in the above embodiment, a protrusion extending in the proximal end direction may be provided on the distal end side inside the hub assembly, and the disc valve may be opened by moving the disc valve to the distal end side. Alternatively, the disc valve may be opened by pressing a separately provided button, and a known disc valve opening part may be employed. When the disc valve is opened, it is preferable that the deformed portion of the disc valve or the moved disc valve closes the flow path that connects the inside and the outside of the hub assembly.

In addition, although the pusher is provided in the above-described embodiment, the pusher can also be not provided by adjusting the dimension from the proximal end to the disc valve with the guide connector or by enlarging the shape of the disc valve in the axial direction. Further, the filter, which is a three-dimensional filtering structure, is directly compressed in the radial direction by the hard members of the connector cover and the guide connector, but another soft member or hard member may be provided between the connector cover and the guide connector to compress the filter in the radial direction.

Fourth Embodiment

Next, a fourth embodiment of the invention will be described. This embodiment is an example in which the hub is not made up of two parts, the guide connector and the connector cover, but is made up of an integral part. Further, the example is about the configuration in which the ventilation path is not provided with a filter, and the ventilation path communicates the region on the distal end side of the disc valve in the inner peripheral surface of the hub and the region on the proximal end side of the disc valve.

Figure 21:
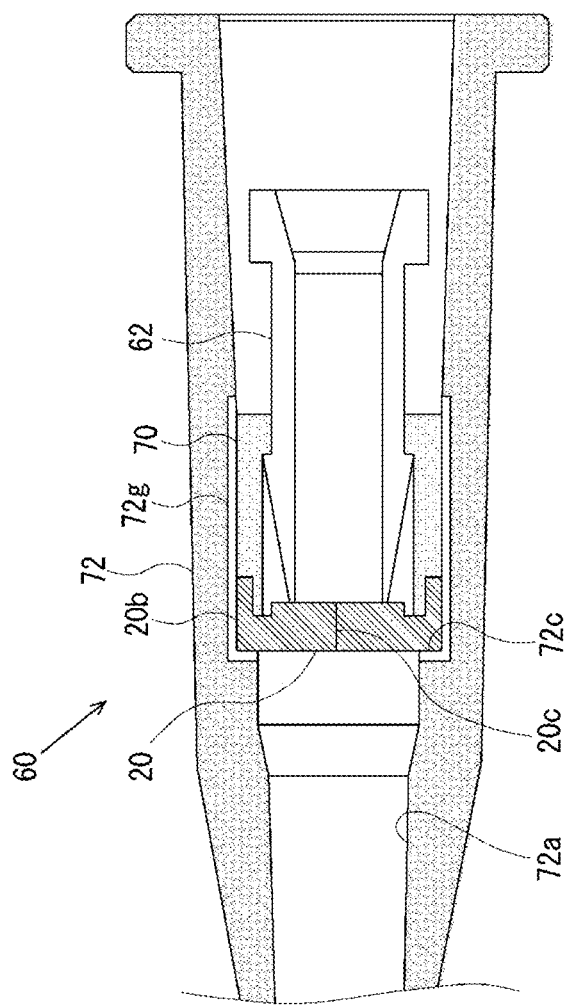
FIG. 21 is a cross-sectional view of a hub assembly according to a fourth embodiment of the invention as seen from a direction perpendicular to an axis.

FIG. 21 is a cross-sectional view of the hub assembly 60 in this embodiment as seen from a direction perpendicular to the axial direction. The hub assembly 60 is provided with a hub 72 that integrates the functions of the connector cover and the guide connector. The inner peripheral surface of the hub 72 forms a liquid flow path 72a. Further, a step is provided by a wall portion 72c at approximately the center in the front-rear direction. The disc valve 20 abuts on the wall portion 72c and fixed inside the hub 60. Further, inside the hub 72, a pusher guide 70 is disposed on the proximal end side of the disc valve 20, and inside the pusher guide 70, a pusher 62 is disposed so as to be movable in the front-rear direction. Since the dimensional relationship and the positional relationship among the pusher 62, the disc valve 20, and the pusher guide 70 are substantially the same as those in the first embodiment, the description thereof is omitted here.

Further, the distal end side of the disc valve 20 in the inner peripheral surface of the hub 72 and the proximal end side of the pusher guide 70 are communicated with each other by a ventilation path 72g. The ventilation path 72g is formed in a groove shape extending in the axial direction between the inner peripheral surface of the hub 72, the outer peripheral surface of the frame portion 20b of the disc valve 20 and the outer peripheral surface of the pusher guide 70, and is provided at four places at 90 degree intervals when seen from the axial direction.

An outer needle unit is configured by fixing the outer needle 14, the outer needle base 14a, and the clamping tube 13 described in the first embodiment to the distal end of the hub assembly 60 having the above structure. Further, an indwelling needle assembly is constructed by inserting an inner needle unit having an inner needle into the outer needle unit.

The usage of the indwelling needle assembly including the hub assembly 60 in this embodiment is also the same as that in the first embodiment. That is, after the indwelling needle assembly is punctured into the blood vessel of a living body, the inner needle unit is pulled out from the outer needle unit to the proximal end side. At that time, for example, the air existing on the distal end side of the disc valve 20 inside the hub 72 is pushed out to the proximal end side by the inflow pressure of blood, flows into the ventilation path 72g, and flows into the ventilation path 16g in the proximal-end direction. As a result, the blood of the living body is smoothly introduced into the hub 72, and so-called "flashback" is more smoothly confirmed by the user.

In the configuration illustrated in FIG. 16, when the connector of the external device is coupled from the rear end side of the hub 72, the connector of the external device abuts on the proximal end of the pusher 62 as in the other embodiments described above. The pusher 62 is moved toward the distal end direction. The pusher 62 is pushed into the slit of the disc valve 20, and the distal end side and the proximal end side of the disc valve 20 in the inner peripheral surface of the hub 72 are communicated with each other through the slit. Then, the pressure of the pump of the external device fluctuates, so that the liquid pumped by the operation of the pump vigorously flows into the ventilation path 72g, and the pressure may act. For this reason, blood easily flows into the ventilation path and remains in the ventilation path, which may cause thrombus in the ventilation path.

On the other hand, also in this embodiment, when the pusher 62 is pushed into the slit 20c of the disc valve 20, a part of the disc portion 20a of the disc valve 20 is configured to close the opening of a ventilation path 72g which is on the distal end side of the disc valve 20 in the inner peripheral surface of the hub 72. As a result, the space on the distal end side and the space on the proximal end side of the partition wall can be made in a non-communication state, and the influence of the pump pressure on the filter can be reduced. Further, the blood pumped by the pump of the external device is not delivered to the opening of the ventilation path with the same momentum, the influence on the filter provided near the opening of the ventilation path can be reduced, the disc valve 20 weakens the momentum of the blood, and the blood can be made hard to flow into the ventilation path.

In addition, in the above-mentioned embodiment, closing the opening of the ventilation path includes a case of closing all of the openings and a case of closing a part of the openings. Further, it includes a case of closing the opening by tightly abutting, and a case of closing the opening with a gap.

OTHER EMBODIMENTS

In another embodiment of the invention, a part of the disc valve 20 may surround the opening of the ventilation path. Alternatively, a part of the disc valve 20 may be deformed so as to come into circumferential contact with the inner surface of the hub closer to the living body side than the opening of the ventilation path. In the embodiment, an annular protrusion having an outer diameter that abuts on the outer peripheral side of the deformed region of the disc portion 20a is provided in a partial outer surface of the pusher 22, so that the annular protrusion deforms the outer peripheral side of the deformed region of the disc portion 20a in the distal end direction to make the outer peripheral side of the deformed region of the disc portion 20a and the inner surface of the hub circumferentially abut with each other. However, a circumferential protrusion may be provided in the surface on the living body side of the disc valve 20, and the protrusion is configured to circumferentially abut on the inner surface of the hub to tightly contact and close the periphery of the opening. In addition, the position and the size of the opening of the ventilation path may be appropriately set to realize the closing of the opening of the ventilation path when the partition wall is deformed. The partition wall is not limited to the disc valve, and the slit is not limited to the elastic body having the linear cut, but may be formed by crushing the hole or by stacking a plurality of members.

The above-described embodiments include a plurality of independent inventions such as a ventilation path mechanism for connecting the inside and the outside of the hub assembly, a mechanism for fixing the filter to a specific position, a ventilation path closing mechanism, a filter pressure resistance mechanism, and the like. Regardless of the form of the hub assembly, it is useful to provide a mechanism in which the partition wall closes the opening of the ventilation path in order to reduce the adverse effect of the pump pressure. Further, regardless of the form of the hub assembly, it is useful to compress the filter provided on the ventilation path in order to reduce the leakage of blood. Further, regardless of the form of the hub assembly, it is useful to provide the filter with a water absorbing swelling body in order to reduce the leakage of blood. These inventions are independent of each other, and, for example, the ventilation path closing mechanism has no particular relation to the position of the filter, and is an independent invention that can reduce the possibility of blood leakage during dialysis treatment by closing the ventilation path even if the filter is not provided.

The above embodiments include a plurality of inventions for solving independent problems such as the ventilation mechanism and the pressure resistance mechanism. Further, the present invention is not limited to the embodiments.

REFERENCE SIGNS LIST 9, 39 guide connector
10, 40 hub assembly
12, 42 outer needle unit
13 clamping tube
14 outer needle
16, 46 connector cover
18, 48 filter cap
20 disc valve
22 pusher
25, 55 filter

What is claimed is:
1. A hub assembly for enabling a predetermined liquid to flow between a living body to be treated or tested and an external device, comprising:
   a substantially cylindrical hub that is connected to a tube from the external device and forms a passage of the liquid;
   a partition wall that is disposed in the passage of the liquid inside the hub;
   a filter that allows gas in the passage of the liquid to pass therethrough and restricts passing of the liquid;
   a ventilation path that communicates with the passage of the liquid and an outside of the hub through the filter, and is able to discharge the gas in the passage of the liquid to the outside by making the air pass through the filter; and
   a filter cap fixed to the hub such that the filter cap does not move relative to the hub, the filter cap having a substantially cylindrical shape centered on a central axis of the hub and covering an area of an outer wall surface of the hub where the filter is arranged, wherein:
      the hub includes a first hub that contacts the partition wall from the proximal end side of the partition wall, and a second hub that sandwiches the partition wall together with the first hub on the distal end side of the partition wall,
      the filter cap is configured as a separate member from the first hub and the second hub,
      an end portion on the partition wall side of an opening of the ventilation path with respect to the passage of the liquid is provided at a place of 10 mm or less on a distal end side with respect to a distal end of the partition wall, and
      the filter cap covers an entire circumference of the outer wall surface of the hub when viewed from a direction of the central axis, with respect to the area where the filter is arranged on the outer wall surface of the hub.

2. A hub assembly for enabling a predetermined liquid to flow between a living body to be treated or tested and an external device, comprising:
   a substantially cylindrical hub that is connected to a tube from the external device and forms a passage of the liquid;
   a partition wall that is provided with a slit disposed in the passage of the liquid inside the hub;
   a filter that allows gas in the passage of the liquid to pass therethrough and restricts passing of the liquid;
   a ventilation path that allows the gas in the passage of the liquid to pass through the filter for ventilation; and
   a filter cap fixed to the hub such that the filter cap does not move relative to the hub, the filter cap having a substantially cylindrical shape centered on a central axis of the hub and covering an area of an outer wall surface of the hub where the filter is arranged, wherein:
      the hub includes a first hub that contacts the partition wall from the proximal end side of the partition wall, and a second hub that sandwiches the partition wall together with the first hub on the distal end side of the partition wall,
      the filter cap is configured as a separate member from the first hub and the second hub,
      when the tube from the external device is connected to the hub, the slit of the partition wall is pushed open to communicate a living body side and an external device side of the partition wall in the passage of the liquid, an opening of the ventilation path for the passage of the liquid on the living body side of the partition wall is provided in a region where a part of the partition wall deformed around the slit reaches when the slit of the partition wall is pushed open, and the filter cap covers an entire circumference of the outer wall surface of the hub when viewed from a direction of the central axis, with respect to the area where the filter is arranged on the outer wall surface of the hub.

3. The hub assembly according to claim 2, wherein, when the slit of the partition wall is pushed open and the living body side and the external device side of the partition wall in the passage of the liquid are made to communicate, a part of the deformed partition wall closes an opening of the ventilation path with respect to the passage of the liquid, and a diameter of the passage of the liquid is 3 mm or more at a position where the opening of the ventilation path with respect to the passage of the liquid is provided.

4. A hub assembly for enabling a predetermined liquid to flow between a living body to be treated or tested and an external device, comprising:

a substantially cylindrical hub that is connected to a tube from the external device and forms a passage of the liquid;

a partition wall that is provided with a slit disposed in the passage of the liquid inside the hub;

a filter that allows gas in the passage of the liquid to pass therethrough and restricts passing of the liquid;

a ventilation path that communicates with the passage of the liquid and an outside of the hub through the filter, and is able to discharge the gas in the passage of the liquid to the outside by making the air pass through the filter; and a filter cap that covers a region in an outer wall surface of the hub where the filter is disposed, wherein:

the hub includes a first hub that contacts the partition wall from the proximal end side of the partition wall, and a second hub that sandwiches the partition wall together with the first hub on the distal end side of the partition wall, the filter cap is fixed to the hub such that the filter cap does not move relative to the hub, the filter cap has a substantially cylindrical shape centered on a central axis of the hub, is configured as a separate member from the first hub and the second hub, and covers an entire circumference of the outer wall surface of the hub when viewed from a direction of the central axis in the area where the filter is arranged on the outer wall surface of the hub.

5. The hub assembly according to claim 4, wherein the filter cap includes a cap ventilation part that allows gas passed through the filter to be discharged to the outside of the filter cap.

6. The hub assembly according to claim 4, wherein the filter has a ring-shaped three-dimensional shape provided between an outer wall surface of the hub and an inner wall surface of the filter cap, and at least one of corners of the outer wall surface of the hub and the inner wall surface of the filter cap, which is in contact with the filter, is rounded.

7. The hub assembly according to claim 4, wherein the filter has a ring-shaped three-dimesional shape provided between an outer wall surface of the hub and an innter wall surface of the filter cap, and at least a part of the filter is compressed and fixed by the outer wall surface of the hub and the inner wall surface of the filter cap, and at least a part of surroundings of the fixed filter includes a storage space for storing a protruding portion of the filter, which protrudes due to the compression of the filter.

8. A hub assembly for enabling a predetermined liquid to flow between a living body to be treated or tested and an external device, comprising:

a substantially cylindrical hub that forms a passage of the liquid;

an openable and closable partition wall that is disposed in the passage of the liquid inside the hub;

a ventilation path that includes an opening in a region on the living body side of the partition wall in the passage of the liquid, communicates the region on the living body side of the partition wall in the passage of the liquid and a region on the external device side of the partition wall in the passage of the liquid or an outside of the hub, and is able to move gas in the region on the living body side of the partition wall in the passage of the liquid to the region on the external device side of the partition wall in the passage of the liquid or the outside of the hub; and a filter cap fixed to the hub such that the filter cap does not move relative to the hub, the filter cap having a substantially cylindrical shape centered on a central axis of the hub and covering an area of an outer wall surface of the hub where the filter is arranged, wherein:

a filter capable of passing gas is disposed in the ventilation path, and the filter is provided with a water absorbing swelling body, the hub includes a first hub that contacts the partition wall from the proximal end side of the partition wall, and a second hub that sandwiches the partition wall together with the first hub on the distal end side of the partition wall, and the filter cap is configured as a separate member from the first hub and the second hub, and covers an entire circumference of the outer wall surface of the hub when viewed from a direction of the central axis, with respect to the area where the filter is arranged on the outer wall surface of the hub.

* * * * *